(12) United States Patent
Batcheller et al.

(10) Patent No.: US 8,425,894 B2
(45) Date of Patent: Apr. 23, 2013

(54) USE OF OLIGOMERS OF LACTIC ACID IN THE TREATMENT OF GYNAECOLOGICAL DISORDERS

(75) Inventors: Greg Batcheller, Brussels (BE); Thomas Hedner, Gallstad (SE); Joergen Johnsson, Helsingborg (SE); Werner Schubert, Askim (SE); Christer Sjoegren, Viken (SE); Olov Sterner, Malmo (SE); Malgorzat Sznitowska, Gdansk (PL)

(73) Assignee: Laccure AB, Helsingborg (SE)

( * ) Notice: Subject to any disclaimer, the term of this patent is extended or adjusted under 35 U.S.C. 154(b) by 480 days.

(21) Appl. No.: 12/594,147

(22) PCT Filed: Mar. 28, 2008

(86) PCT No.: PCT/EP2008/002505
§ 371 (c)(1),
(2), (4) Date: Mar. 1, 2010

(87) PCT Pub. No.: WO2008/119518
PCT Pub. Date: Oct. 9, 2008

(65) Prior Publication Data
US 2011/0020265 A1 Jan. 27, 2011

(30) Foreign Application Priority Data
Mar. 30, 2007 (DK) .................................. 2007 00508

(51) Int. Cl.
*A61K 31/765* (2006.01)
*A61K 31/225* (2006.01)
*A61P 31/00* (2006.01)
*A61P 15/02* (2006.01)

(52) U.S. Cl.
USPC ......... 424/78.37; 514/547; 694/285; 694/358

(58) Field of Classification Search ............... 424/78.37; 514/547
See application file for complete search history.

(56) References Cited

U.S. PATENT DOCUMENTS

| 4,431,427 | A | * | 2/1984 | Lefren et al. .................. 604/285 |
| 6,369,116 | B1 | | 4/2002 | Wong et al. |
| 2002/0177624 | A1 | | 11/2002 | Hanna et al. |
| 2005/0107464 | A1 | | 5/2005 | Nagato et al. |
| 2005/0271726 | A1 | * | 12/2005 | Crum ............................ 424/486 |

FOREIGN PATENT DOCUMENTS

| JP | 2000072680 | A | | 3/2000 |
| JP | 2004359583 | A | | 12/2004 |
| JP | 2006232909 | A | | 9/2006 |
| WO | 9745066 | A1 | | 12/1997 |
| WO | 03016259 | A2 | | 2/2003 |
| WO | 2004090014 | A1 | | 10/2004 |
| WO | 2004096204 | A1 | | 11/2004 |
| WO | 2006001766 | A1 | | 1/2006 |
| WO | WO2006/001766 | | * | 1/2006 |

OTHER PUBLICATIONS

Andersch et al., "Bacterial Vaginosis and the Effect of Intermittent Prophylactic Treatment with an Acid Lactate Gel", Gynecologic and Obstetric Investigation, vol. 30, No. 2, pp. 114-119 (1990).
Database WPI Week 200023 Derwent Publications Ltd., London, GB; AN 2000-266538 XP002484792 & JP 2000 072680 A (Shumeido KK) Mar. 7, 2000.
Database WPI Week 200474 Derwent Publications Ltd., London, GB; AN 2004-757959 XP002484793 & WO 2004/090014 A (Amato Pharm Prod Ltd) Oct. 21, 2004.
Database WPI Week 199750 Derwent Publications Ltd., London, GB; AN 1997-539683 XP002484794 & JP 09 227388 A (Naganushi T) Sep. 2, 1997.
Database WPI Week 200664 Derwent Publications Ltd., London, GB; AN 2006-617508 XP002484795 & JP 2006 232909 A (Univ Tokai GH) Sep. 7, 2006.
Database WPI Week 200505 Derwent Publications Ltd., London, GB; AN 2005-048515 XP002484796 & JP 2004 359583 A (Amato Pharm Prod Ltd.) Dec. 24, 2004.
"Hemorrhoids", Manual of Medicine, Diagnosis and Therapy, "The Merk Manual", Moscow, Mir. 1997, vol. 1, p. 583—with English Translation.
J. Sanford et al., "Antimicrobial Therapy", Pocket Guide, Praktika,Moscow, pp. 21-22, 25-26 (1996)—with English Translation.
G.R. Burmester et al., "Visual Immunology", M. BINOM 2007, p. 214 (2006)—with English translation.

* cited by examiner

*Primary Examiner* — Anoop Singh
*Assistant Examiner* — Anna Falkowitz
(74) *Attorney, Agent, or Firm* — Edwards Wildman Palmer LLP; Peter F. Corless; Christine C. O'Day

(57) ABSTRACT

Use of the one or more oligomers of lactic acid with the following formula (I) wherein n is an integer from 2 to 25 such as, e.g., from 2 to 20, from 3 to 25, from 3 to 20, from 2 to 15, from 3 to 15, from 2 to 10, from 3 to 10, from 4 to 10, or from 4 to 9 or a lactic acid oligomeric product for the prophylaxis and/or treatment of a disease or condition that benefit of an acidic environment especially a gynaecological infection such as a bacterial infection, such as bacterial vaginosis, unspecific colpitis, senile colpitis, cervicitis, and urethritis, a fungal infection, such as candidosis (*Candida albicans*), cryptococcosis, actinomycosis, or a viral infection, such as Human Immunodefiency Virus (HIV), Herpes Simplex Virus (HSV), Human Papilloma Virus (HPV).

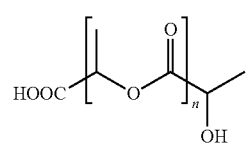

(I)

10 Claims, 17 Drawing Sheets

Figure 1:
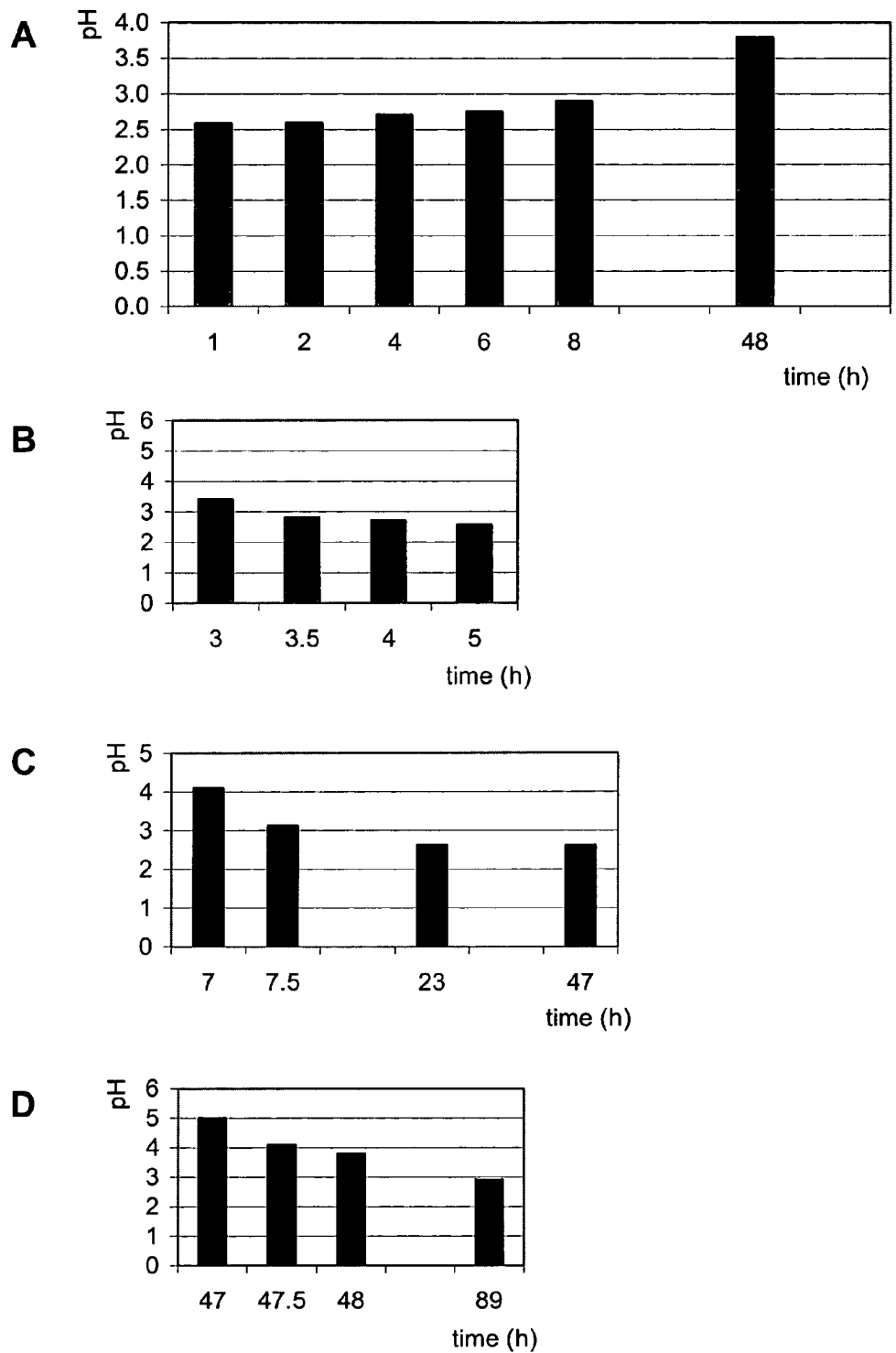

A   The profile of release of lactic acid from pessaries

B   changes of pH in acceptor liquid (pessaries)

A

B

USE OF OLIGOMERS OF LACTIC ACID IN THE TREATMENT OF GYNAECOLOGICAL DISORDERS

FIELD OF INVENTION

The present invention describes use of oligomers of lactic acid (OMLA) for the prophylaxis and/or treatment of gynaecological infections, such as microbial or viral infections, notably bacterial vaginosis. Moreover, the oligomeric products of the invention can be used in the treatment or prophylaxis of any disease or condition where an acid pH below about 4.0 or 4.5 is desired or as excipients releasing an acid during a prolonged period of time in order to maintain a suitably low pH in the environment. The invention also relates to novel oligomers of lactic acid as well as to novel oligomeric products containing specific mixtures of specific lactic acid oligomers. Specifically, the present invention relates to oligomers of lactic acid in the range from dimer to dodecamer and the use thereof. The oligomers are normally presented as a formulation e.g. in the form of a device or a kit.

BACKGROUND OF THE INVENTION

Gynaecological or reproductive tract infections generally refer to three different types of infection which affect the reproductive tract. Endogenous infections include bacterial vaginosis and candidosis, which result from an overgrowth of organisms which are normally present in the vagina. The endogenous infections represent the most common form of lower gynaecological tract infections (LGTIs) worldwide, and they can be easily treated. However they commonly reappear, which is a major medical problem. Iatrogenic infections represent a second group which occur when the infectious agent (a bacterium or other micro-organism) is introduced into the reproductive tract through various routes such as menstrual regulation, induced abortion, IUD insertion or during parturition. Finally. sexually transmitted infections (STIs) are caused by microorganisms such as viruses, bacteria, or parasitic microorganisms that are transmitted through sexual activity with an infected partner. Among the STIs there are several serious diseases such as HIV, chlamydia trachomatis, condyloma accuminata, syphilis and *Neisseria gonorrhea*. STIs can affect both men and women, but a transmission from mothers to children during pregnancy and childbirth may also occur.

Bacterial vaginosis (BV) is the most frequent endogenous infection and also the most common medical condition of the female genital tract. BV is linked to increased complications in pregnancy, and may be involved in the pathogenesis of pelvic inflammatory disease and women's risk of acquiring HIV. Still many questions remain about its aetiology, which complicates the management of recurrent infections.

BV is an overgrowth of anaerobic bacteria and a lack of normal *Lactobacilli flora*, which results in an imbalance of normal vaginal flora. During pregnancy BV is associated with poor perinatal outcome and a cause of preterm birth. Identification and treatment of BV may reduce the risk of such consequences. A range of therapeutic options has been tested in order to manage or prevent recurrences of BV.

It is not yet known whether frequent episodes of BV are the result of re-infection or relapse. The association of BV with sexual behaviour suggests that BV is sexually transmitted and that additional episodes may be due to re-infection. However, evidence do not support the theory of sexual transmission and re-infection and several studies evaluating risk factors for repeated episodes of BV suggests it is due to relapse. Women developing early recurrence tend to complain of abnormal discharge at the end of therapy. Moreover, asymptomatic women who consider themselves cured after treatment, continued to have abnormal vaginal flora. Furthermore, the more severe the abnormality the earlier is usually the recurrence.

The value of bacteriotherapy, using harmless bacteria to displace pathogenic organisms remain unresolved.

Psychosexual symptoms with lack of libido and anxiety about infection may be reported by some women as a consequence of recurrent episodes of bacterial vaginosis and associated malodour. However, concurrent treatment of the male partner does not reduce the rate of BV relapse. However, condom use with male sexual partners may help to reduce the risk of relapse of bacterial vaginosis. Hormonal contraception use does not increase the incidence of bacterial vaginosis, while women with an intrauterine contraceptive device or system in situ may have an increased risk of BV.

Vaginal Discharge

Vaginal discharge is a common presenting symptom, which may be physiological or pathological. While BV remains one of the most common diagnoses in women attending genitourinary medicine clinics, vulvovaginal candidiasis is another common infective cause of vaginal discharge that affects about 75% of women at some time during their reproductive life. Approximately 50% of cases of bacterial vaginosis are asymptomatic and the true prevalence of this condition in the community is uncertain. *Lactobacilli* colonising the vaginal epithelium may have a role in defence against infection. Normal vaginal flora (*lactobacilli*) maintains the vaginal pH between 3.8 and 4.4. The quality and quantity of vaginal discharge may be altered in the same woman over time. There is a wide variation in vaginal discharge and each woman has her own sense of normality and what is acceptable or excessive.

The main problem of the pathogenic vaginal discharge is the malodour. This odour has the characteristics of a foul fishy smell which is characteristic for bacterial vaginosis and caused by amines, mainly trimethylamine. Other clinical manifestations may be excessive discharge and a sense of unfreshness.

DETAILED DESCRIPTION OF THE INVENTION

As appears from the above there is a need for developing formulations that are suitable for use in management of gynaecological infections, notably bacterial vaginosis, and that enable a less frequent administration compared to the treatment regimens known today that requires daily or more than daily administration.

To this end, the present inventors have found that oligomers of lactic acids are suitable for use. On the one hand the oligomers release lactic acid once they are contacted with an aqueous medium and on the other hand the oligomers serve as a lactic acid depot, i.e. not all lactic acid is released immediately; the release of lactic acid is dependent on the oligomer in question.

In a main aspect, the present invention provides the use of one or more oligomers of lactic acid for the preparation of a formulation for the prophylaxis and/or treatment of gynaecological infections.

In other aspects the one or more oligomers of lactic acid may be used in the treatment or prophylaxis of any conditions which benefit from a low pH e.g. in the diseased environment. Thus, the OMLA with or without combination with lactate may be used in the treatment of prophylaxis for diseases or disorders affecting the skin or mucosa. A preparation containing OMLA with or without combination with lactate may also be used as an excipient for various topical and mucosal preparations for medical, dental or veterinary use. Further to that, OMLA with or without combination with lactate may be used as an ingredient in products intended for cosmetic or cosmeceutical use.

Examples of oral mucosal application where suitable preparations is of medical value is e.g., aphte (aphtous stomatitis), or other types of oral mucosal lesions due to bacterial infections, viral infections, fungal infections, or other medical reasons like e.g. leucoplacia or "Burning Mouth Syndrome". In addition, OMLA with or without combination with lactate may also be used in saliva replacement treatments or preparations.

Rectal preparations of OMLA with or without combination with lactate may be used in diseases or disorders such as haemorroids, anal fissures, pruritus ani or proctitis.

In the field of dermatology, there are several areas where skin preparations or applications of OMLA with or without combination with lactate added to known registered or applicable pharmaceutical agents or ingredients and may be of beneficial use. Examples of such skin diseases or disorders are; wounds, eczema, atopic dermatitis, psoriasis, acne, rosacea, urticaria, pruritus, light dermatosis, hyperhidrosis, alopecia, as well as bacterial infections, viral infections, fungal infections, and ectoparasites.

In dental practice, OMLA with or without combination with lactate may be used as an ingredient or excipient in dental cream as well as a combination treatment or an ingredient or excipient for treatments or prophylaxis of caries and/or parodontitis and or halitosis An additional use of OMLA with or without combination with lactate may be in gastroenterology, where beneficial effects may be seen in acid disorders such as achylia.

In another main aspect, the present invention relates to novel oligomers of lactic acids. Accordingly, the present invention provides an oligomer of lactic acid with the following formula I

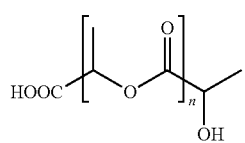

wherein n is an integer from 2 to 25 such as, e.g., from 2 to 20, from 3 to 25, from 3 to 20, from 2 to 15, from 3 to 15, from 2 to 10, from 3 to 10, from 4 to 10, or from 4 to 9. In specific embodiments, n may be higher dependent on the application and the time period for releasing lactic acid. Accordingly, in those cases where a very long release time of lactic acid is desired, n may be up to 50 such as, e.g. from 20 to 50, from 20 to 30, from 30 to 40 or from 40 to 50 (the lower range giving a release period that is lower than the higher range). The novel oligomers of lactic acids in substantial pure form (i.e. the specific oligomer is present in a concentration of 90% or more) do not encompass the tetramer of lactic acid manufactured as described in the following: To a solution of lactic acid tetramer tert-butyl ester (0.6982 g) (1.9268 mmol) in methylene chloride (25 ml) was dropped a mixed solution of trifluoroacetic acid (2.5 ml) and methylene chloride (2.5 ml), followed by stirring at room temperature for 1 hour after the end of dropping; a saturated sodium hydrogen carbonate solution (30 ml) was added to adjust the pH of water layer to pH 8, and then a saturated ammonium chloride (50 ml) was added thereto to adjust the pH of water layer to pH 6; the resultant was extracted three times with diethyl ether (100 ml); the extraction solution contained almost all impurities and a small amount of the substance of interest; to the remaining water layer was dropped 1N hydrochloric acid (5 ml) cooled at 0° C., so as to adjust the pH of water layer to pH 2-3; the layer was extracted three times with methylene chloride (150 ml); at this time, the pH changed, and therefore 1N hydrochloric acid cooled at 0° C. was used to keep the pH of the water layer at pH 2-3; the resultant was dried over anhydrous magnesium sulphate day and night, concentrated, and isolated by column chromatography (developing solvent: hexane:diethyl ether=1:4) to obtain lactic acid tetramer (0.2047 g) (yield:34.7%) as a colourless oil.

As mentioned above, the present invention relates to novel oligomers of lactic acid. Such compounds are normally difficult to obtain as 100% pure compounds, but will normally contain a mixture of the main oligomer together with lactic acid oligomers with different degrees of oligomerization dependent on the synthesis conditions. Thus, in the present context, the term "novel oligomer of lactic acid" is intended to denote an oligomer with a specific degree of oligomerization, wherein the concentration of this specific oligomer is at least about 90% w/w. However, the present invention also relates to novel oligomeric products containing a mixture of lactic acid oligomers. Such mixtures are normally obtained directly from the synthesis process and, as seen from the Examples herein, contain one or more main oligomers together with a number of oligomers of smaller and larger size. In the oligomeric products obtained without any purification step to remove oligomers of higher or lower molecular weight than the main product, the main oligomers are normally present in a concentration of at least about 4% w/w. As can be seen from the Examples herein, the higher the mean molecular weight is, the wider is the molecular weight distribution of the product obtained. Thus, in those cases, where the weight average molecular weight is from about 400 to about 700, then the main oligomer(s) individually is/are present in a concentration of at least about 10% w/w (range 10-25%), whereas when the weight average molecular weight of the product increase to from about 700 to about 1,000 then the main oligomer(s) individually is/are present in a concentration of at least about 7% w/w (range 7-12%), and when the weight average molecular weight increase to from about 1,000 to about 1,700 then the main oligomer(s) individually is/are present in a concentration of at least about 4.4% w/w (range 4.4-7).

Moreover, as seen from the examples herein, in those cases where the weight average molecular weight is from about 400 to about 700, the concentration of the main oligomers ($HL_2$-$HL_6$ or $HL_3$-$HL_6$ where $HL_2$ is the dimer, $HL_3$ is the trimer etc.) is at least about 30% (in the specific examples the range is form about 30 to about 65%). For oligomeric products in the range of from about 700 to about 1,000, the concentration of the main oligomers ($HL_2$-$HL_8$ or $HL_3$-$HL_7$) is at least about 35% (in the specific examples the range is from about 35 to about 65%).

As mentioned above, a variety of oligomeric products with different mixtures of individual oligomers can be obtained. The selection of a specific oligomeric product depends on its intended use. As demonstrated in the examples herein, the release of lactic acid from the oligomeric products depends on the oligomerization of lactic acid. Thus, an oligomeric product having a weight average molecular weight in the lower end tends to release lactic acid faster than an oligomeric product having a higher molecular weight. Accordingly, if a fast onset of action is required, then the choice is an oligomeric product having a weight average molecular weight of corresponding to a range of $HL_3$-$HL_6$. Moreover, from the examples herein it is seen that such composition can lead to an effect for at least about 8 hours (based on in vitro experiments, see FIG. 1, a low pH can be maintained for 1-2 days). If a more prolonged release of lactic acid is desired, an oligomeric product with a higher weight average molecular weight is chosen such as, e.g., an oligomeric product having a weight average molecular weight corresponding to a range of $HL_6$-$HL_{12}$ or $HL_6$-$HL_{10}$ (medium release—in vitro duration for at least about 48 hours) or $HL_{10}$-$HL_{25}$ for even slower release. As seen from the examples herein, an advantage by using oligomeric products that have a certain molecular weight distribution is that it is possible to obtain both a fast onset of action (due to the content of small oligomers) and a more sustained action (due to the content of oligomers of higher molecular weight).

Accordingly, in specific embodiments the present invention relates to oligomeric products having the following compositions:

i) An oligomeric product, wherein the total concentration of $HL_2$-$HL_5$ is at least about 50% w/w such as at least about 60% w/w. In a preferred embodiment, the concentration is from about 60% w/w to about 70% w/w and the average weight molecular weight is from about 350 to about 500. Due to the content of relatively small oligomers in relatively high concentration such a product has a fast onset of action and a relatively short duration of action (8-12 hours or more, but likely not more than a couple of days)

ii) An oligomeric product, wherein the total concentration of $HL_2$-$HL_5$ is at least about 40% w/w. In a preferred embodiment, the concentration is from about 40% w/w to about 50% w/w and the average weight molecular weight is from about 450 to about 600. Due to the content of relatively small oligomers such a product has a fast onset of action and due to its content of higher oligomers it has short-medium duration of action (1-2 days or more, but likely not more than 4-6 days).

iii) An oligomeric product, wherein the total concentration of $HL_2$-$HL_5$ is at least about 30% w/w. In a preferred embodiment, the concentration is from about 30% w/w to about 40% w/w and the average weight molecular weight is from about 500 to about 750. Due to the content of relatively small oligomers such a product has a fast onset of action and due to its content of higher oligomers it has medium duration of action (2 days or more, but likely not more than 1 week).

iv) An oligomeric product, wherein the total concentration of $HL_3$-$HL_8$ is at least about 35% w/w. In a preferred embodiment, the concentration is from about 35% w/w to about 65% w/w and the average 700 to about 1,000. Due to the content of relatively small oligomers (although in a lower concentration than in the products i)-iii) above, such a product is expected to have a certain immediate action and due to its content of higher oligomers it has a longer duration of action (more than 2 days).

The oligomeric products i)-iv) mentioned above all have a certain molecular weight distribution in order to enable both a fast onset of action (i.e. within the first hours after application) and a more prolonged action. Accordingly, the polydispersity index of such products (discussed below) is normally from about 1.2 to about 1.5 of from about 1.3 to about 1.4.

Other specific embodiments are mentioned in the Examples herein.

A more narrow molecular weight distribution can be obtained by subjecting the oligomeric products obtained to a purification process such as, e.g. gel filtration. Accordingly, the present invention also relates to such products, where the main oligomer is present in a concentration of 15% w/w or more such as, e.g., 20% w/w or more, 25% w/w or more or wherein the concentration of the main oligomers (i.e. the total concentration of the individual main oligomers) is 45% w/w or more such as, e.g., 60% w/w or more or 75% w/w or more. Such relatively pure oligomeric products may also be used in combination to obtain a desired release of lactic acid as discussed above.weight molecular weight is from about 700 to about 1,000. Due to the content of relatively small oligomers (although in a lower concentration than in the products i)-iii) above, such a product is expected to have a certain imidiate action and due to its content of higher oligomers it has a longer duration of action (more than 2 days).

The oligomeric products i)-iv) mentioned above all have a certain molecular weight distribution in order to enable both a fast onset of action (i.e. within the first hours after application) and a more prolonged action. Accordingly, the polydispersity index of such products (discussed below) is normally from about 1.2 to about 1.5 of from about 1.3 to about 1.4.

Other specific embodiments are mentioned in the Examples herein.

A more narrow molecular weight distribution can be obtained by subjecting the oligomeric products obtained to a purification process such as, e.g. gel filtration. Accordingly, the present invention also relates to such products, where the main oligomer is present in a concentration of 15% w/w or more such as, e.g., 20% w/w or more, 25% w/w or more or wherein the concentration of the main oligomers (i.e. the total concentration of the individual main oligomers) is 45% w/w or more such as, e.g., 60% w/w or more or 75% w/w or more. Such relatively pure oligomeric products may also be used in combination to obtain a desired release of lactic acid as discussed above.

In a further main aspect, the present invention relates to a formulation comprising one or more oligomers of lactic acid (notably a novel oligomeric product) and one or more pharmaceutically acceptable excipients.

In a further main aspect, the present invention relates to a device for the delivery of a therapeutically effective amount of a formulation for the prophylaxis and/or treatment of a gynaecological infection.

In a further main aspect, the present invention relates to a kit for the prophylaxis and/or treatment of gynaecological infections, which comprises at least a first and a second component, wherein the first component comprises a formulation and the second component comprises instructions for use of the formulation.

In a further main aspect, the present invention relates to a package or container for storage of a kit.

In yet another main aspect, the present invention relates to a method for the prophylaxis and/or treatment of a gynaecological infection, the method comprising administering to a subject in need thereof an effective dose of one or more oligomers of lactic acid, optionally in form of a formulation.

In one aspect, the invention provides a formulation of one or more oligomers of lactic acid, which has acidifying properties over a prolonged period of time.

Bacterial Vaginosis; its Background and Epidemiology

BV is characterised by a malodorous vaginal discharge, a vaginal pH of more than 4.5, a positive amine test, and a thin homogeneous white fluor, and the presence of clue cells microscopically and on occasion vaginal burning or itching.

The vaginal flora is altered from the normal *lactobacilli* (LB) dominant to flora with reduced numbers of LB and an overgrowth of *Gardnerella vaginalis, Mycoplasma hominis*, and anaerobic bacteria such as *streptococci, Prevotella* spp, and *Mobiluncus* spp.

Bacterial vaginosis is commonly diagnosed by Amsel's criteria if 3 of the following 4 criteria are present: 1; a vaginal pH higher then 4.5, 2; the presence of clue (vaginal epithelial) cells in the vaginal fluid, 3; a thin grey or white homogenous discharge, 4; or a positive KOH "whiff" test (release of fishy odour upon the addition of 10% potassium hydroxide to the vaginal fluid)

Some predisposing factors have been shown to increase the risk of BV, such as younger age, black ethnicity, douching, smoking, and the IUD contraception. Several reports have linked BV with sexual behaviour, a recent change of sexual partner, as well as multiple partners.

The invention will now be further described and illustrated by reference to the following examples, which have been carefully selected in order to encompass the invention. Accordingly, they should not be construed as limiting the invention in any way.

Definitions

In relation to the substance per se, the terms "oligomer of lactic acid" and "OMLA" are used as synonyms and are intended to mean one or more oligomers of lactic acid with formula I, wherein n is an integer from 2 to 20 such as, e.g., from 3 to 20, from 2 to 15, from 3 to 15, from 2 to 10, from 3 to 10, from 4 to 10, or from 4 to 9. The novel oligomers of lactic acids does not encompass a tetramer of lactic acid manufactured as described in the following: To a solution of lactic acid tetramer tert-butyl ester (0.6982 g) (1.9268 mmol) in methylene chloride (25 ml) was dropped a mixed solution of trifluoroacetic acid (2.5 ml) and methylene chloride (2.5 ml), followed by stirring at room temperature for 1 hour after the end of dropping; a saturated sodium hydrogen carbonate solution (30 ml) was added to adjust the pH of water layer to pH 8, and then a saturated ammonium chloride (50 ml) was added thereto to adjust the pH of water layer to pH 6; the resultant was extracted three times with diethyl ether (100 ml); the extraction solution contained almost all impurities and a small amount of the substance of interest; to the remaining water layer was dropped 1N hydrochloric acid (5 ml) cooled at 0° C., so as to adjust the pH of water layer to pH 2-3; the layer was extracted three times with methylene chloride (150 ml); at this time, the pH changed, and therefore 1N hydrochloric acid cooled at 0° C. was used to keep the pH of the water layer at pH 2-3; the resultant was dried over anhydrous magnesium sulphate day and night, concentrated, and isolated by column chromatography (developing solvent: hexane:diethyl ether=1:4) to obtain lactic acid tetramer (0.2047 g) (yield:34.7%) as a colourless oil.

However, in relation to use of oligomers of lactic acid it is envisaged that small structural variations of the oligomers do not affect their ability to release lactic acid. Accordingly, derivatives of the oligomers, wherein the terminal carboxylic acid and/or hydroxyl group has been derivatized e.g. to an ester, an amide, a thio ester (for the carboxylic acid) or an ether (for the hydroxyl group) are envisaged to be suitable for use in accordance with the invention. Accordingly, derivatives of oligomers of lactic acid with the following formula II

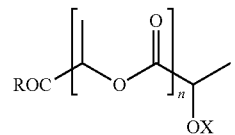

(II)

wherein n is as defined herein before for formula (I) and R is H, $R^1R^2N—$, $R^1O—$, or $R^1S—$, and $R^1$, $R^2$ and $R^3$ are the same or different and selected from H, $C_1$-$C_6$ alkyl including methyl, ethyl, propyl, isopropyl, butyl, isobutyl, tert. butyl, pentyl, hexyl, or aryl including benzyl, and pharmaceutically acceptable salts thereof, and X is H or alkyl including methyl, ethyl, propyl, isopropyl, butyl, isobutyl, tert. butyl, pentyl, hexyl, or acyl, $—OCR^4$, wherein $R^4$ is selected from H, $C_1$-$C_6$ alkyl including methyl, ethyl, propyl, isopropyl, butyl, isobutyl, tert. butyl, pentyl, hexyl, or aryl including benzyl, and pharmaceutically acceptable salts thereof, provided that R is not OH when X is H, may also be used in combination or as substitution for the lactic acid oligomers of formula (I), or in oligomeric lactic acid products as described herein.

By the term "antimicrobial" is intended to mean an effect that destroys or inhibits the growth of microbes, such as bacteria (e.g. Group B *Streptococcus*), fungi, viruses, or parasites. By the term "antibacterial" is intended to mean an effect that destroys or inhibits the growth of bacteria. By the term "antifungal" is intended to mean an effect that destroys or inhibits the growth of fungi. By the term "antiviral" is intended to mean an effect that destroys or inhibits the ability of a virus to replicate and, hence, inhibits its capability to multiply, reproduce or grow.

By the term "weight average molecular weight" or "$M_w$" is intended to be a description of the molecular weight of a polymer. The weight average molecular weight is calculated as: $M_w=\Sigma_i(N_iM_i^2)/\Sigma_i(N_iM_i)$ wherein $N_i$ is the number of molecules of molecular weight $M_i$. Intuitively, if the weight average molecular weight is w, and you pick a random monomer, then the polymer it belongs to will have a weight of w on average. The weight average molecular weight can be determined by e.g. mass spectrometry, NMR spectroscopy, light scattering, small angle neutron scattering (SANS), X-ray scattering, and sedimentation velocity.

By the term "number average molecular weight" or "$M_n$" is intended mean a determination of the molecular weight of a polymer. The number average molecular weight is the common, mean, average of the molecular weights of the individual polymers. It is determined by measuring the molecular weight of n polymer molecules, summing the weights, and dividing by n: $M_n=\Sigma_i(N_iM_i)/\Sigma_i(N_i)$ wherein $N_i$ is the number of molecules of molecular weight $M_i$. The number average molecular weight of a polymer can be determined by e.g. mass spectrometry, NMR spectroscopy, vapor pressure osmometry, end-group titration, and colligative properties.

By the term "polydispersity index" is intended to mean a measure of the distribution of molecular weights in a polymer sample, which is determined as the ratio of the weight average molecular weight to the number average molecular weight of a polymer.

By the term "oligomeric product" is intended to mean a product containing two or more oligomers of lactic acid, i.e. a mixture of oligomers with different degrees of oligomerization. As appears from the description and the examples herein, oligomeric products are normally obtained by use of the synthesis method and the polydispersity index is used as a measure for how broad or narrow the molecular weight distribution is. As explained herein, it is normally an advantage to have oligomers of different molecular weights in the product as it e.g. can give rise to a fast release of lactic acid from the low molecular weight oligomers and a more sustained and prolonged release from the higher molecular weight polymers. In this manner it is possible to design an oligomeric product with a desired release profile.

By the term "formulation" is intended to mean a composition comprising one or more OMLAs together with one or more pharmaceutically acceptable excipients or such which can be accepted for topical use to the skin or mucosa. A formulation according to the invention may be presented in any suitable form, notably for administration to the vagina including vaginal administration. The term "formulation" is also used for the preparation which does not contain any added excipients, besides OMLA, but is prepared in a way to conform requirements for application to the mucosa.

By the term "antiadhesion agent" is intended to mean any agent that will reduce the adhesion properties of gynaecological pathogenic microbial organisms or virus and in particular agents that will cause such organism or virus to disadhere.

By the term "adhesiveness" is intended to mean the effect that provides or promotes adhesion or "stickiness" to a surface, such as the mucosa. For the adhesion to the mucosa the term "mucoadhesiveness" can be also used.

By the term "vagitorium" is intended to mean a drug, which is introduced to the vagina where the active ingredients are released and absorbed and will act on the mucosa; and the term "pessary" is used as a synonym hereof.

Oligomers of Lactic Acid

In one embodiment relating to oligomers of lactic acid per se, the invention comprises one or more oligomers of lactic acid with formula I, wherein n is an integer as defined herein in connection with formula (I). The novel oligomers of lactic acids in pure form does not encompass a tetramer of lactic acid manufactured as described in the following: To a solution of lactic acid tetramer tert-butyl ester (0.6982 g) (1.9268 mmol) in methylene chloride (25 ml) was dropped a mixed solution of trifluoroacetic acid (2.5 ml) and methylene chloride (2.5 ml), followed by stirring at room temperature for 1 hour after the end of dropping; a saturated sodium hydrogen carbonate solution (30 ml) was added to adjust the pH of water layer to pH 8, and then a saturated ammonium chloride (50 ml) was added thereto to adjust the pH of water layer to pH 6; the resultant was extracted three times with diethyl ether (100 ml); the extraction solution contained almost all impurities and a small amount of the substance of interest; to the remaining water layer was dropped 1N hydrochloric acid (5 ml) cooled at 0° C., so as to adjust the pH of water layer to pH 2-3; the layer was extracted three times with methylene chloride (150 ml); at this time, the pH changed, and therefore 1N hydrochloric acid cooled at 0° C. was used to keep the pH of the water layer at pH 2-3; the resultant was dried over anhydrous magnesium sulphate day and night, concentrated, and isolated by column chromatography (developing solvent: hexane:diethyl ether=1:4) to obtain lactic acid tetramer (0.2047 g) (yield:34.7%) as a colourless oil.

In one embodiment relating to the use of oligomers of lactic acid, the invention comprises one or more derivatives of oligomers of lactic acid has the above-mentioned formula II, wherein n, R and X are as defined before Oligomers of lactic acid are chains of lactic acids coupled to each other by ester links between the carboxylic acid moiety in one with the secondary alcohol function in another. The number of monomers joined is between 2 and typically 20. The formulation for prophylaxis and/or treatment of bacterial vaginosis may also include the use of a carboxylic acid such as benzoic acid or acetic acid, dicarboxylic acids such as malonic acid, compounds having both a carboxylic acid and a hydroxyl group (e.g. salicylic acid), carbonates, sulphates or variant in which the end group is formula II is R, wherein R is $R^1R^2N$, $R^1O-$, or $R^1S-$, $R^1$, $R^2$ and $R^3$ are the same or different and selected from H, C1-C6 alkyl including methyl, ethyl, propyl, isopropyl, butyl, isobutyl, tert. butyl, pentyl, hexyl, or aryl including benzyl, as well as pharmaceutically acceptable salts thereof.

The compounds prepared by the method of the present invention include all combinations of optical isomers of the oligomers of lactic acid compounds according to the present invention (e.g., R and S enantiomers, D- and L-forms), as well as racemic, diastereomeric, meso and other mixtures of such isomers.

In addition, the oligomers of lactic acid may be transformed to its corresponding esters, amides, thioesters, or salts. The salt of oligomers of lactic acid may be any pharmaceutically acceptable salt such as sodium, potassium, calcium, magnesium or ammonium, or trometamole salt. In addition, the oligomers of lactic acid may be found as complexes with metals or with macromolecules.

The physical appearance of the oligomeric product depends on the mean molecular weight ranging from a fluid, semi-solid and to a solid product. The lower molecular weight, the more fluid the product is. The water-solubility is also dependent on the average molecular weight. The less oligomerization of the lactic acid, the higher is the water-solubility. These properties can also be used in the design of a suitable composition. Thus if e.g. a fast dissolving product is desired with fast release properties, then an oligomeric product with a relatively low weight average molecular weight should be chosen (e.g. $HL_3$-$HL_6$), whereas if a less soluble product is desired and a longer release time, then an oligomeric product with a higher weight average molecular weight should be chosen (e.g. $HL_5$-$H_{10}$ or even higher). Moreover, the individual oligomeric product can be chosen dependent on the final dosage form. Thus, e.g. for a gel formulation or other liquid or semi-solid compositions, the choice of oligomeric product could suitably be among the fluid, semi-fluid oligomeric products, whereas for solid compositions such as, e.g., tablets or capsules, the solid oligomeric products could be more convenient.

In one embodiment the oligomer of lactic acid has a water solubility of at least 1 weight percent, such as 0.1 to 50, 1 to 50 weight percent, 1 to 30 weight percent, or 5 to 30 weight percent at room temperature. The water solubility of the oligomers of lactic acid is dependent on the length of the oligomer. Moreover, the solubility may be in increased in diluted alkaline solutions.

In one embodiment the one or more oligomers of lactic acid has a $M_w$ of from 400 to 2,000 g/mol. In a specific embodiment the one or more oligomers of lactic acid has a $M_w$ of from 380 to 760 g/mol, such as from 400 to 700 g/mol, from 450 to 650 g/mol, from 500 to 650 g/mol, from 550 to 625 g/mol, or from 550 to 600 g/mol. The oligomer may be substantially pure as defined herein or, more typically, the one or more oligomers of lactic acid is contained in an oligomeric product with a certain polydispersity. The polydispersity is typically about 1.2 to 1.5 such as, e.g., from about 1.3 to about 1.4, but the product may also be purified to a lower polydispersity, if desired.

In an embodiment of the invention, the one or more oligomers of lactic acid has a $M_n$ of from 250 to 1,500 g/mol. In a specific embodiment the $M_n$ is from 250 to 760 g/mol such as, e.g., from 380 to 760 g/mol, such as from 400 to 700 g/mol, from 450 to 650 g/mol. In a further embodiment, the $M_n$ is from 500 to 600 g/mol, from 525 to 600 g/mol, or from 525 to 575 g/mol. In the examples herein are given examples of corresponding values of $M_w$ and $M_n$ and polydispersity index.

In another specific embodiment the one or more oligomers of lactic acid has a $M_w$ of from 700 to 2,000 g/mol. In a specific embodiment the one or more oligomers of lactic acid has a $M_w$ of from 700 to 1,700 g/mol, such as from 700 to 1,000 g/mol, from 1,000 to 1,500 g/mol, from 1,500 to 2,000 g/mol. The oligomer may be substantially pure as defined herein or, more typically, the one or more oligomers of lactic acid are contained in an oligomeric product with a certain polydispersity. The polydispersity is typically about 1.2 to 1.5 such as, e.g., from about 1.3 to about 1.5, but the product may also be purified to a lower polydispersity, if desired.

In another specific embodiment the one or more oligomers of lactic acid has a $M_n$ of from 500 to 1,500 g/mol. In a specific embodiment the one or more oligomers of lactic acid has a $M_n$ of from 500 to 1,300 g/mol, such as from 600 to 1,100 g/mol. In another embodiment, the $M_n$ is 1,000 to 1,500 g/mol or from 1,000 to 1,200 g/mol. The oligomer may be substantially pure as defined herein or, more typically, the one or more oligomers of lactic acid is contained in an oligomeric product with a certain polydispersity. The polydispersity is typically about 1.2 to 1.5 such as, e.g., from about 1.3 to about 1.5, but the product may also be purified to a lower polydispersity, if desired.

In one embodiment the polydispersity index of the oligomers of lactic acid according to the present invention is less than 1.8 such as less than 1.7. More typically, the polydispersity index is 1.5 or less, such as less than 1.4, or from 1.2, to 1.4. The more purified the product is the lower is the polydispersity index. Accordingly, for some embodiments of the invention the polydispersity index is less than 1.2 or less than 1.1. For pure oligomers the polydispersity index may be less than 1.08, less than 1.06, less than 1.04, less than 1.02, or less than 1.01.

In one embodiment the one or more oligomers of lactic acid or the oligomeric product have an inherent viscosity at 25° C. in the range of $10^{-3}$ to $10^{12}$ Pa·s, such as $10^{-1}$ to $10^9$ Pa·s, 1 to $10^5$ Pa·s, when determined by a rheometer.

In one embodiment the one or more oligomers of lactic acid release lactic acid over a time period of at least 4 hours, at least 8 hours, at least 12 hours, such as at least 16 hours, at least 20 hours, at least 24 hours, at least 36 hours, at least 2 days, at least 3 days, at least 4 days, at least 5 days, at least 6 days, or at least 7 days when exposed to water at room temperature.

As discussed herein before, a mixture of oligomers are obtained and can be used as such. In such mixtures normally at the most 10-20% w/w of the individual oligomers are present.

Specific Oligomeric Products of the Invention are:

i) an Oligomeric Product Containing
10-20% w/w of $HL_2$
15-25% w/w of $HL_3$
10-20% w/w of $HL_4$ and
8-15% w/w of $HL_5$ ii) an Oligomeric Product Containing
10-15% w/w of $HL_2$
15-25% w/w of $HL_3$
10-15% w/w of $HL_4$ and
10-15% w/w of $HL_5$ iii) an Oligomeric Product Containing
7-15% w/w of $HL_2$
7-15% w/w of $HL_3$
7-15% w/w of $HL_4$ and
8-15% w/w of $HL_5$ iv) an Oligomeric Product Containing
2.5-10% w/w of $HL_2$
4-15% w/w of $HL_3$
5-15% w/w of $HL_4$ and
5-15% w/w of $HL_5$ v) an Oligomeric Product Containing
2.5-7.5% w/w of $HL_2$
5-10% w/w of $HL_3$
5-12% w/w of $HL_4$ and
5-12% w/w of $HL_5$ vi) an Oligomeric Product Containing
5-15% w/w of $HL_3$
5-15% w/w of $HL_4$
5-15% w/w of $HL_5$
5-10% w/w of $HL_6$ and
5-15% w/w of $HL_7$ vii) an Oligomeric Product Containing
5-10% w/w of $HL_3$
5-10% w/w of $HL_4$
5-10% w/w of $HL_5$
5-10% w/w of $HL_6$ and
5-10% w/w of $HL_7$ viii) an Oligomeric Product Containing
2.5-7.5% w/w of $HL_3$
5-10% w/w of $HL_4$
5-10% w/w of $HL_5$
5-10% w/w of $HL_6$ and
5-15% w/w of $HL_7$ Other embodiments of the invention are more purified products such as the following.

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a trimer of lactic acid (n=2).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a tetramer of lactic acid (n=3).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a pentamer of lactic acid (n=4).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a hexamer of lactic acid (n=5).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a heptamer of lactic acid (n=6).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a octamer of lactic acid (n=7).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a nonamer of lactic acid (n=8).

In another embodiment at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a decamer of lactic acid (n=9).

Acidifying Properties

A low pH of the vagina is due to production of lactic acid by lactobacilli metabolism, and as well as the conversion of glycogen to lactic acid by oestrogenised vaginal epithelial cells. In culture *lactobacilli* acidify their growth medium to a pH of 3.2-4.8. At that pH range a steady state of equilibrium develops where the acidity becomes auto-inhibitory. Anaerobes grow poorly at pH 4.5 or less. In vitro studies show that the concentrations of BV associated bacteria increase with increasing vaginal pH. However, it has been found that lactic acid and low pH caused more mashed inhibitory effect of these bacteria than hydrogen peroxide. However, when there is a rise in vaginal pH, such as after sex and during menses, bacterial overgrowth could occur. Interestingly, a low pH seems to be important for adherence of *lactobacilli* to the epithelial cells. BV can also be produced by inoculating BV associated bacteria into a healthy vagina as shown in the initial work by Gardner and Dukes (Gardner H L, Dukes C D. *Haemophilus vaginalis* vaginitis. Am J Obstet Gynecol 1955; 69:962-76).

Thus, the exact mechanism for the onset of BV remains unsolved. BV is associated with a reduced number of *lactobacilli* (LB) and a lower hydrogen peroxide production. There is a rise in the vaginal pH, and the overgrowth of BV associated organisms. Currently, it is not known what causes the reduction in hydrogen peroxide producing strains of *lactobacilli* in BV.

In other words, the main goal to prevent or treat BV is to keep the vaginal pH at 4.5 or less. This will prevent overgrowth of pathogenic bacteria until the normal LB are re-established and able to maintain the pH.

Intermittent pH lowering therapy, on an episodic or prophylactic basis, may be considered to prevent or treat recurrent BV.

The invention includes a method as well as a formulation for prophylaxis and/or treatment of bacterial vaginosis, by providing a therapeutically effective amount of one or more oligomers of lactic acid or derivatives thereof or a combination of such oligomers of lactic acid or derivatives thereof.

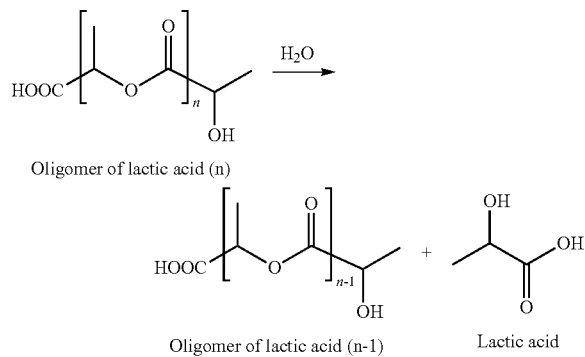

Oligomer of lactic acid (n)

Oligomer of lactic acid (n-1)        Lactic acid

The formulation may also consist of a therapeutically effective combination one or more oligomers of lactic acid and lactate.

Adhesiveness

Mucoadhesion (or bioadhesion) is defined as the process whereby synthetic and natural macromolecules adhere to various mucosal surfaces in the body. If a molecule possesses mucoadhesive properties or if such mucoadhesive materials are incorporated as constituents into pharmaceutical formulations, local drug action or drug absorption by mucosal cells may be enhanced or prolonged. Moreover, if mucoadhesive properties are present in the molecule or if mucoadhesive constituents are incorporated, drug release and action may be increased at the site of application for an extended period of time.

OMLA itself possesses some mucoadhesive properties, however in combination with other polymers present in a formulation, used as a matrix or coating, OMLA exhibits a pronounced mucoadhesiveness or at least some mucoadhesiveness depending on the molecular weight (see Table I below). As can be seen below, the mucoadhesiveness for the OMLA gels, patches and vagitoria are judged as (3) pronounced to (4) very pronounced.

This property is inherent in the OMLA molecule and clearly demonstrable as shown in the chemical and preformulation experiments made. The extent of the mucoadhesivness for OMLA is so pronounced that there will be no need for adding further mucoadhesive constituents to the formulations during the galenic development of vagitories or pessaries based on OMLA.

For synthetic polymers, such as the cellulose derivatives, chitosans, carbopols and carbomers, the mechanism of bio/mucoadhesion is the result of a number of different physicochemical interactions. This will also be the likely mechanism(s) for the pronounced mucoadhesiveness which is seen for OMLA.

TABLE I

Mucoadhesive properties of OMLA formulations

| | Fluid | Gel | Patch | Vagitoria |
|---|---|---|---|---|
| Lactic acid, 85% purity | 0 | — | — | — |
| OMLA (mainly tetramer to octamer) | — | 3 | 4 | 3 |
| OMLA (mainly pentamer to decamer) | — | 4 | 4 | 4 |

It should be noted that lactic acid is a liquid and present only in fluid form, while the OMLA become gradually more semisolid to solid with extending the length of the molecule. In the compositions comprising OMLA, OMLA is not present in fluid form but only in semisolid or solid form.

Mucoadhesiveness (or bioadhesiveness) is given according to a 5 graded VAS scale, where 0 denotes no mucoadhesive properties and 4 very pronounced mucoadhesive properties.

In a specific embodiment of the present invention the one or more oligomers of lactic acid have a mucoadhesiveness of at least 3 such as, e.g. at least 4 or 5 on a graded VAS scale.

Management of Bacterial Vaginosis

When using oral or vaginal preparations of metronidazole and clindamycin, women will have an initial 80-90% response to treatment but there will be 15-30% relapse within 3 months. When considering the association between *lactobacilli*, hydrogen peroxide production, vaginal pH, and overgrowth of BV associated bacteria, adjustment of only one of these may help some women with recurrent BV, but it may be insufficient to resolve all cases.

Although there is a well known inter-relation between *lactobacilli*, hydrogen peroxide production, vaginal pH, and overgrowth of BV associated bacteria, the initiating factor for BV remains unresolved.

Treatment only focusing on one aspect of this inter-relation may benefit some women with recurrent BV, but a combined approach is superior. Since bacterial vaginosis can also be asymptomatic, recurrence often cannot be differentiated from treatment failure. Thus, recurrent bacterial vaginosis may be prevented by using effective therapy for the initial episode.

In one embodiment the one or more oligomers of lactic acid are used for the preparation of a formulation for the prophylaxis and/or treatment of gynaecological infections. In a further embodiment the gynaecological infection is a bacterial infection, such as bacterial vaginosis, unspecific colpitis, senile colpitis, cervicitis, and urethritis. In a further embodiment the gynaecological infection is a fungal infection, such as candidosis (*candida albicans*), cryptococcosis, actinomycosis. In a further embodiment the gynaecological infection is a viral infection, such as Human Immunodefiency Virus (HIV), Herpes Simplex Virus (HSV), Human Papilloma Virus (HPV).

Formulations

An OMLA according to the present invention or used according to the present invention is normally presented as a pharmaceutical formulation, i.e. OMLA is present in the formulation together with one or more pharmaceutically acceptable excipients.

The pharmaceutically acceptable excipients may be selected from the group consisting of carriers, diluents, binders, disintegrating agents, flow-improving agents, pH-adjusting agents, stabilising agents, viscosity adjusting agents, preservatives, gelling or swelling agents, surfactants, emulsifying agents, suspending agents, bases for suppositories, vagitories or pessaries, bases for creams, ointments, gels, lotions, shampoos, foam, sprays and the like. The specific choice of pharmaceutically acceptable excipients depends on the specific form or the formulation, e.g. the dosage form. A person skilled in the art can find guidance e.g. in Remington's Pharmaceutical Sciences (Gennaro, Alfonso R., ed., 18. ed., 1990, xvi, Mack, ISBN: 0-912734-04-3).

The final formulation may also comprise one or several pharmaceutically acceptable salts such as phosphate, succinate, lysinate, acetate, cypionate, valerate, hemisuccinate, butyrate, or trometamole salt alone or in combination. The amount of lactate polymer or derivative included in each dose preparation may range from 0.01 mg to 50 g per dose unit but is preferentially 0.5 mg to 5 g. The formulation of one or more oligomers of lactic acid will restore normal physiological pH in the vagina. This will reduce the number of anaerobic bacteria which cause the characteristic unpleasant vaginosis malodour through trimethylamine production.

In one embodiment according to the present invention the formulation comprises i) one or more oligomers of lactic acid or derivative thereof as defined in any of items 1-40, ii) a combination of one or more oligomers of lactic acid or derivative thereof as defined in any of items 1-40, or iii) a combination of i) and/or ii) and/or lactic acid for the prophylaxis and/or treatment of a microbial infection according to any of items 1-4.

In one embodiment the formulation comprises at least 0.01% w/w of the one or more oligomers of lactic acid. In another embodiment the formulation comprises from about 0.02% to 100% w/w such as, e.g. from about 0.1% to about 95% w/w, from about 1% to about 95% w/w, from about 5% to about 95% w/w, from about 10% to about 90% w/w, from about 15% to about 90% w/w, from about 15% to about 50% w/w or from about 15% to about 40% w/w of the one or more oligomers of lactic acid.

In one embodiment the one or more oligomers of lactic acid release lactic acid over a time period of at least 8 hours, at least 12 hours, such as at least 16 hours, at least 20 hours, at least 24 hours, at least 36 hours, at least 2 days, at least 3 days, at least 4 days, at least 5 days, at least 6 days, or at least 7 days when exposed to water at room temperature.

In one embodiment the formulation is designed for vaginal administration. In another embodiment the formulation is for intravaginal or transvaginal administration.

In one embodiment the formulation is a solid, semi-solid or liquid formulation. In another embodiment according to the present invention the galenic formulation is in the form of a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal shaum, vaginal disc, semipermeable packaging and any combination thereof.

In one embodiment the pharmaceutical agent of the formulation according to the invention is incorporated into the device as a controlled release drug delivery system.

In one embodiment the formulation comprises glycogen or precurors or derivatives thereof, e.g. to serve as a source of sustenance for *Lactobacillus*.

In another embodiment the formulation comprises probiotics in the form of live micro-organisms such as *Lactobacillus acidophilus* or similar species, which when administered in adequate amounts confer a health benefit on the host, resulting in a *Lactobacilli*-reestablishment of the *Lactobacillus*-dominant vaginal flora.

In a further embodiment the pH-adjusting agents provide a pH lower than 5, such as lower than 4 in order to obtain a more rapid restoration of the acid milieu to optimize the therapeutic response and the regrowth of *Lactobacilli*.

A formulation according to the invention may be in any suitable form. The specific form should be chosen dependent on the specific administration route. Thus, for oral administration (to the GI tract), semi-solid or solid compositions are preferred such as, e.g., solid dosage forms (e.g. tablets, capsules, sachets), powders, granules, beads, pellets etc. For topical administration or administration to the oral cavity gel, creams, ointments, lotions, powders, patches, tooth paste, mouth wash etc. may be suitable. A person skilled in the art will find guidance e.g. in Remington's Pharmaceutical Sciences for the preparation of such forms and for selection of suitable pharmaceutically acceptable excipients.

In a specific aspect the formulation is designed to be administered to the vagina. In such cases the following dosage forms are suitable:

Viscosity-Adjusting or Adhesion Promoting Agents

In one embodiment of the invention the formulation further comprises one or more pharmaceutically acceptable excipients selected from the group consisting of cellulose derivatives such as hydroxypropyl methylcellulose (HPMC), methyl cellulose, hydroxyethyl cellulose (HEC), hydroxypropyl cellulose (HPC), ethyl hydroxyethyl cellulose, carboxymethyl cellulose and sodium carboxymethyl cellulose (Na CMC), starch derivatives such as moderately cross-linked starch, acrylic polymers such as carbomer and its derivatives (Polycarbophyl, Carbopol®, etc); polyethylene oxide (PEO), chitosan (poly-(D-glucosamine); natural polymers such as gelatin, sodium alginate, pectin, scleroglucan, tragacanth, gellan, xanthan gum or guar gum, poly co-(methylvinyl ether/maleic anhydride), microcrystalline cellulose/Avicel®), and crosscarmellose. In another embodiment of the invention the concentration of the pharmaceutically acceptable excipient is in the range 0.05 to 10 weight percent, such as 0.1 to 5 weight percent, of the formulation. In yet another embodiment the one or more pharmaceutically acceptable excipients are vaginal mucoadhesive promoting agents and/or viscosity-adjusting agents.

Antimicrobial Properties

A microbiological study throughout the menstrual cycle, have shown that the concentration of non-LB species was higher at menses. Thus, there is a potential for bacterial overgrowth at that time, since there is instability of the vaginal flora.

The idea of adding antibacterial components to the preparation is that pathogenic bacteria produce hydrolytic enzymes which degrade the vaginal mucine lining. This effect of the pathogens damages the normal protective vaginal mucous lining.

The formulation may also include one or more antimicrobial agents such as antibiotics, such as clindamycin or metronidazol, essential oils, such as tea tree oil, cations or elements, such as Hg, Cu, Pb, or Ag, polyene antimycotic, imidazole, triazole, allyamines, echinocandin, aciclovir, amantadine, alcohols, quarternary ammmonium compounds, boric acid, chlorhexidine gluconate, hydrogen peroxide, urea hydrogen peroxide, iodine, mercurochrome, octenine dihydrochloride, phenolic (carbolic acid) compounds, sodium chloride, sodium hypochlorite, nonoxynol as well as combinations and/or mixtures of such agents. An oxygenating compound such as $H_2O_2$ will provide an unfavourable milieu for the pathogenic anaerobic bacteria characteristic of the bacterial vaginosis. In addition, some oxygenating compounds such as $H_2O_2$ may also add antibacterial properties for the pathogens. *Lactobacilli*, which themselves produce $H_2O_2$, are less adversely affected of e.g. $H_2O_2$.

The antimicrobial agent may be used in appropriate concentrations recognised by a person skilled in the art. The concentration of antimicrobial agent may be more than 0.01 weight percent, such as is in the range 0.01 to 50 weight percent, such as 0.01 to 25 weight percent, from 0.05 to 25 weight percent, 0.1 to 10 weight percent, 0.5 to 5 weight percent of the formulation.

In one embodiment according to the invention the formulation further comprises an antibacterial agent selected from the group consisting of clindamycin, tetracycline, amoxicillin, ampicillin, erythromycin, doxycycline, lumefloxacin, norfloxacin, afloxam, ciproflaxin, azitromycin, cefltoxine, and chlorchinaldol.

In another embodiment according to the invention the formulation further comprises a formulation of one or more antibacterial agents for the prophylaxis and/or treatment of gynaecological infections as defined herein.

In another embodiment according to the invention the antibacterial agent is selected from the group consisting of clindamycin, tetracycline, amoxicillin, ampicillin, erythromycin, doxycycline, lumefloxacin, norfloxacin, afloxam, ciproflaxin, azitromycin, cefltoxine.

In another embodiment according to the invention the amount of antibacterial agent is in the range from 5 mg to 1000 mg per dose.

In another embodiment according to the invention the antibacterial agent selected from the group consisting of tetracycline, doxycycline, azithromycin, or erythromycin is incorporated into a tampon.

In another embodiment according to the invention the formulation further comprises one or more broad spectrum antibiotic agent.

In a further embodiment according to the invention the broad spectrum antibiotic agent is selected from the group consisting of clindamycin, tetracycline, amoxicillin, ampicillin, erythromycin, doxycycline, lumefloxacin, norfloxacin, afloxam, ciproflaxin, azitromycin cefitoxine for the prophylaxis and/or treatment of gonorrhea or chlamydial infections. In yet a further embodiment according to the invention the amount of broad spectrum antibiotic agent is in the range from 100 mg to 3000 mg per dose.

In a further embodiment according to the invention the broad spectrum antibiotic agent is selected from the group consisting of tetracycline, amoxicillin, ampicillin, lumefloxacin, norfloxacin, afloxam, ciproflaxin, azithromycin or cefitoxine for prophylaxis and/or treatment of gonorrhea. In a further embodiment according to the invention the amount of broad spectrum antibiotic agent is in the range from 400 mg to 3000 mg per dose.

In a further embodiment according to the invention the formulation further one or more broad spectrum antibiotic agents selected from the group consisting of tetracycline, doxycycline, and erythromycin for treatment of chlamydial infections. In yet a further embodiment the amount of broad spectrum antibiotic agent is in the range from 100 mg to 2000 mg per dose. In yet a further embodiment the formulation is in the form of a tampon.

In one embodiment according to the invention the formulation further comprises an antichlamydial agent selected from the group consisting of tetracycline, doxycycline, and erythromycin.

In one embodiment according to the invention the formulation further comprises an antifungal agent selected from the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole. In another embodiment the amount of antifungal agent per dose is in the range from 0.1 mg to 2000 mg for treatment of candidiasis. In a further embodiment one or more antifungal agents selected from the group consisting of ketoconazole, miconazole and metronidazole and optionally, the agent is incorporated into a tampon.

In one embodiment according to the invention the formulation further comprises a spermicidal agent In one embodiment according to the invention the formulation according to any of items 60-64, which further comprises an antiviral agent selected from the group consisting of acyclovir, femciclovir, valacyclovir, and AZT.

In one embodiment according to the invention the formulation according to any of the items 60-63, wherein the formulation further comprises an antiviral agent. In another embodiment the antiviral agent is selected from the group consisting of acyclovir, femciclovir, valacyclovir, and AZT. In a further embodiment the amount of antiviral agent is in the range from 100 mg to 1200 mg per dose. In yet a further embodiment the antiviral agent is acyclovir and is incorporated into a tampon.

In one embodiment according to the invention the formulation according to any of items 65-66 which further comprises an trichomonicidal or parasiticidal agent selected from the group consisting of metronidazole and clotrimazol.

In one embodiment according to the invention the formulation according to any of the items 65-67, wherein the formulation further comprises metronidazole for treatment of trichomoniasis. In another embodiment the amount of metronidazole is in the range from 10 mg to 750 mg per dose.

Antiadhesion Agents

The formulation may further comprise one or more antiadhesion agents. *Lactobacilli* which confer the favourable acidifying properties in the vaginal milieu are not adhered to the vaginal mucosa. However pathogenic fungi are adhered to the mucosa and pathogenic bacteria may be in contact with the mucosa and degrade the protective lining of the normal healthy vaginal mucosa. This may enhance the risk of recurrence of the vaginosis in susceptible patients. Thus, a formulation includes one or several compounds that prevent such mucoadhesion by pathogens may be beneficial for the prophylaxis, prevention and treatment of bacterial vaginosis. The current invention may include one or several carrier core material which prevents the mucoadhesion of pathogenic microorganisms, preferentially anaerobic bacteria and fungi. Antiadhesion agents may be agents that serve as either a barrier preventing adhesion or as an agent that causes already adhered microorganisms to disadhere. Examples of antiadhesion agents causing disadherence may be mannose, lactose, xylitol, and other sugar alcohols. The final formulation may consist of combinations and/or mixtures of several compounds, each in effective amounts when used alone or together.

In one embodiment of the invention the antiadhesion agent is selected from the group consisting of mannose, lactose, xylitol, and other sugar alcohols.

In another embodiment of the invention the amount of antiadhesion agent is in the range 0.01 to 10 weight percent, such as 0.1 to 5 weight percent, of the formulation.

Surfactants

In one embodiment according to the present invention the formulation comprises one or more surfactants selected from the group consisting of sodium lauryl sulphate, polysorbates, bile acids, bile salts, lecithin, phospholipids, methyl laurate, oleic acid, oleyl alcohol, glycerol monoleate, glycerol dioleate, glycerol trioleate, glycerol monostearate, glycerol monolaurate, phospho lipids, propylene glycol monolaurate, sodium dodecyl sulphate, sorbitan ester, salt of cholic acid, cholanic acid, poloxamer, Cremophor, and other polyoxyethylated lipids, and any combination thereof.

In a further embodiment according to the present invention the concentration of the surfactant is in the range 0.01 to 10 weight percent, such as 0.1 to 5 weight percent, of the formulation.

In one embodiment the pharmaceutically acceptable excipient of the formulation according to the invention is a lipophilic or hydrophilic carrier. Examples of lipophilic carriers are waxes, oils, isopropyl myristate, solid triglycerides, and cocoa butter. Examples of hydrophilic carriers are glycerol, propylene glycol, polyoxyethylene glycol.

In another embodiment the formulation according to the invention is for intravaginal delivery and comprises one or more lipophilic or hydrophilic carriers and one or more mucoadhesive agents in total concentrations in the range from 60 to 90% w/w and from 5 to 25% w/w, respectively.

In another embodiment the formulation according to the invention is for transvaginal delivery and comprises one or more lipophilic or hydrophilic carriers, one or more mucoadhesive agents, and one or more penetration enhancers or sorption promoters in total concentrations in the range from 60 to 90% w/w, from 5 to 25% w/w, and from 5 to 20% w/w, respectively.

In another embodiment the formulation further comprises one or more lipophilic carriers of semi-synthetic glycerides of saturated fatty acids of 8-18 carbon atoms.

In another embodiment the formulation further comprises the hydrophilic carrier polyethylene glycol of a molecular weight from 400 to 6000. In a further embodiment the concentration of polyethylene glycol is in the range from 60 to 90% w/w.

In another embodiment the formulation further comprises the mucoadhesive agents alginate, pectin, or hydroxypropyl methylcellulose. In a further embodiment the concentration of hydroxypropyl methylcellulose is in the range from 5 to 20% w/w. In yet a further embodiment the penetration enhancer is a surfactant, bile salt, or ethoxyglycol. In yet a further embodiment the concentration of ethoxyglycol is in the range from 5 to 30% w/w.

In another embodiment according to the present invention the formulation comprises one or more oligomers of lactic acid, one or more derivatives thereof, or a combination of one or more oligomers of lactic acid and one or more derivatives thereof in admixture with a pharmaceutically acceptable and non-toxic excipient comprising from about 60 to 90% w/w of lipophilic or hydrophilic carrier and from about 5 to about 25% w/w of mucoadhesive agent for intravaginal delivery, or from about 60 to about 90% w/w of lipophilic or hydrophilic carrier, from about 5 to about 25% w/w of mucoadhesive agent and from about 5 and 20% w/w of penetration enhancer for transvaginal delivery.

In another embodiment according to the present invention the formulation further comprises a lipophilic carrier of semi-synthetic glyceride of saturated fatty acids of 8-18 carbon atoms, wherein the hydrophilic carrier is polyethylene glycol of a molecular weight from 400 to 6000 in the range from 60 to 90% w/w, and wherein the mucoadhesive agent is alginate, pectin or hydroxypropyl methylcellulose, wherein the concentration of hydroxypropyl methylcellulose is in the range from 5 to 20% w/w; and wherein the penetration enhancer is a surfactant, bile salt or ethoxyglycol, wherein the amount of ethoxyglycol is in the range from 5 to 30% w/w.

Device

In one embodiment the formulation of oligomers of lactic acid according to the present invention may be a device for the prophylaxis and/or treatment of gynaecological microbial bacterial infections, which delivers a therapeutically effective amount of one or more oligomers of lactic acid or derivatives thereof or a combination of one or more oligomers of lactic acid or derivatives thereof intravaginally or transvaginally to uterus or general circulation through a vaginal mucosa, to a subject in need thereof.

In one embodiment the present invention comprises a device for the delivery of a formulation as defined herein for the prophylaxis and/or treatment of a gynaecological infection as defined herein.

In another embodiment according to the present invention the device is intravaginal.

In another embodiment according to the present invention the formulation comprised in the device is administered intravaginally or transvaginally.

In one embodiment the formulation is a solid, semi-solid or liquid formulation. In another embodiment according to the present invention the galenic formulation is in the form of a tampon, vagitorium, vaginal cup, vaginal insert, vaginal patch, vaginal ring, vaginal sponge, vaginal spray, vaginal powder, vaginal rod, vaginal shaum, vaginal disc, semipermeable packaging and any combination thereof.

In another embodiment according to the present invention the pharmaceutical agent is incorporated into the device as a controlled release drug delivery system.

Kit

In one embodiment the formulation of oligomers of lactic acid according to the present invention may be in a kit for the prophylaxis and/or treatment of gynaecological infections as defined herein, which comprises at least a first and a second component, wherein the first component comprises a formulation as defined herein and the second component comprises instructions for use of the formulation.

In another embodiment the first component of the kit comprises a formulation as defined herein and the second component comprises means for administration of the formulation.

In a further embodiment a further third component of the kit comprises instructions for use of the formulation.

In another embodiment the kit may comprise a formulation is in the form of a vaginal device and the means for administration is an applicator.

Package

In one embodiment the present invention comprises a package or container for storage of a kit as defined herein.

Method of Treatment

In one aspect the present invention comprises a method for the prophylaxis and/or treatment of a gynaecological infection, the method comprising administering to a subject in need thereof an effective dose of one or more oligomers of lactic acid as defined herein, optionally in form of a formulation as defined herein.

In another aspect the present invention comprises a method for the management, prophylaxis and/or treatment of odour from vaginal discharge, the method comprising administering to a subject in need thereof an effective dose of one or more oligomers of lactic acid ad defined herein, optionally in form of a formulation as defined herein.

In yet another aspect the present invention comprises a method for the management, prophylaxis and/or treatment of odour from vaginal discharge, the method comprising administering to a subject in need thereof an effective dose of one or more oligomers of lactic acid ad defined herein, optionally in form of a formulation as defined herein, and wherein the formulation comprises a sanitary device.

LEGEND OF FIGURES

FIG. 1. OMLA 12 (dialysis sac)—changes of pH. When OMLA (substance) is placed in a dialysis bag, due to diffusion (OMLA and LA from degradation) pH of the outside aqueous compartment decreases. The pH change occurs for a long time; despite of replacing water outside of the dialysis bag after 3, 7 and 47 h. A) pH 1 h after replacing the liquid. B), C), and D) pH change through the periods between the exchange of water outside of the dialysis bag.

Figure 2:
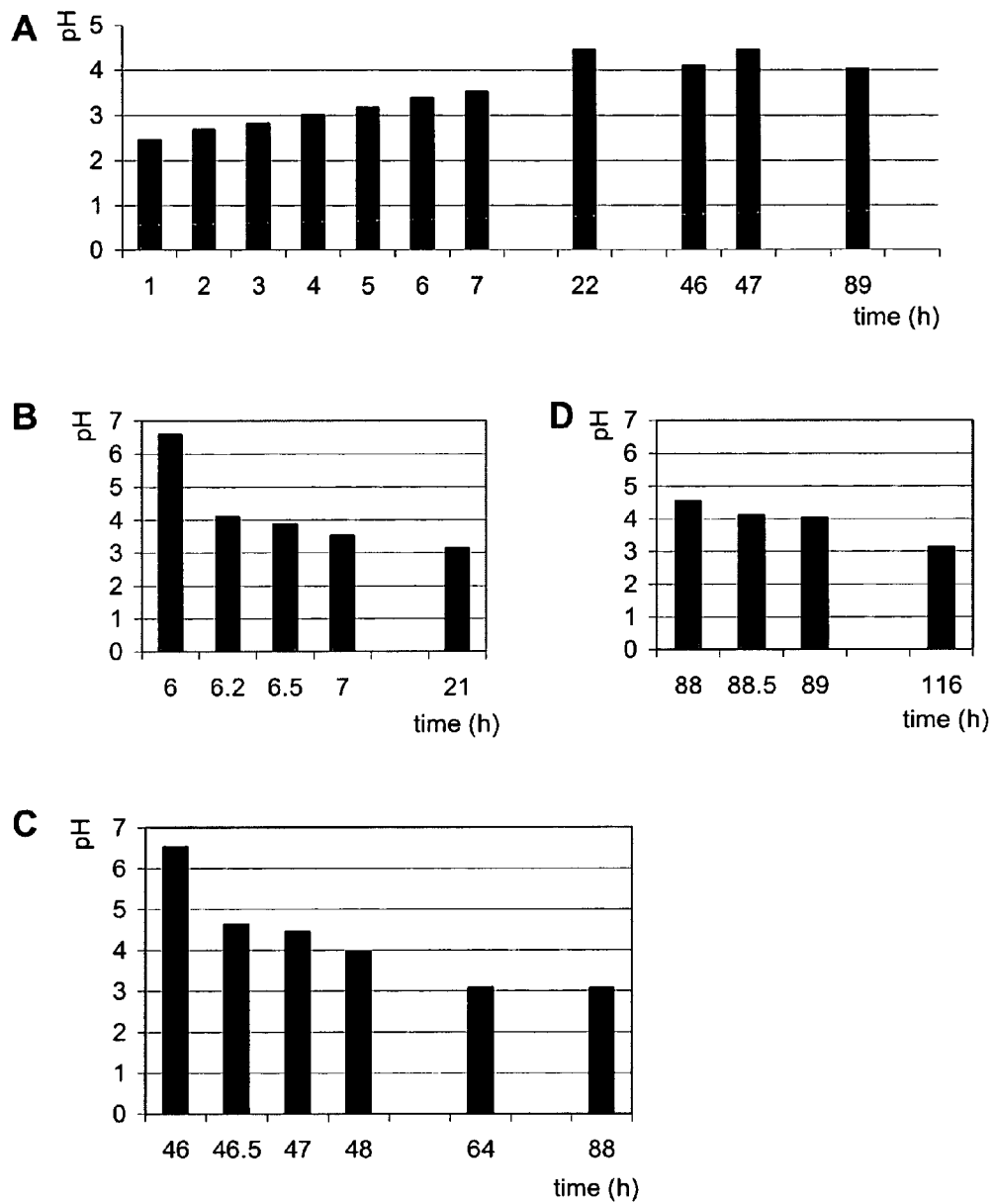

FIG. 2. OMLA 31 (dialysis sac)—changes of pH. This is the same type of the experiment as FIG. 1, but with OMLA 31. The water was exchanged after 6, 46 and 88 hours. Less low-molecular components are present and the effect is weaker and slower as expected. FIG. 2A represents the pH value 1 h after replacing the liquid, and FIG. 2B-2D show pH change through the periods between the exchange of water outside of the dialysis bag.

Figure 3:
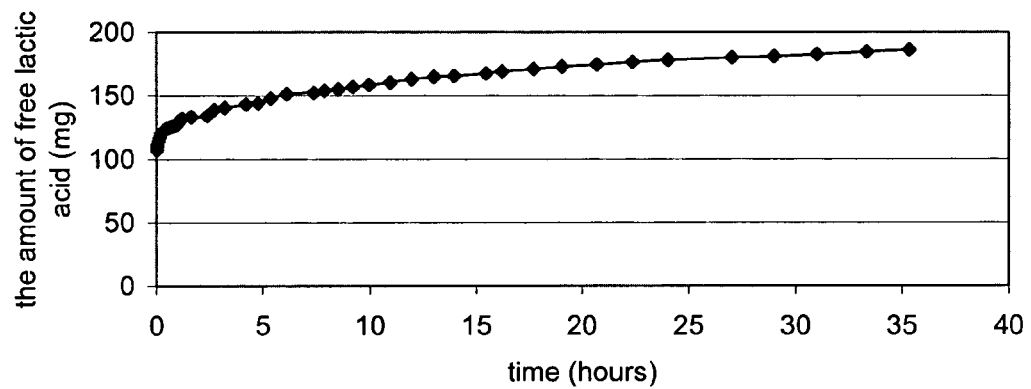

FIG. 3. The profile of release of free lactic acid from OMLA 31 (0.209 g) determined by titration with KOH using magnetic stirring in water at 20° C. The figure presents the quantity of acids (OMLA of low molecular weight and LA) dissolved in water. Half of the OMLA is probably of low molecular weight, whereas the rest dissolves slowly.

Figure 4:
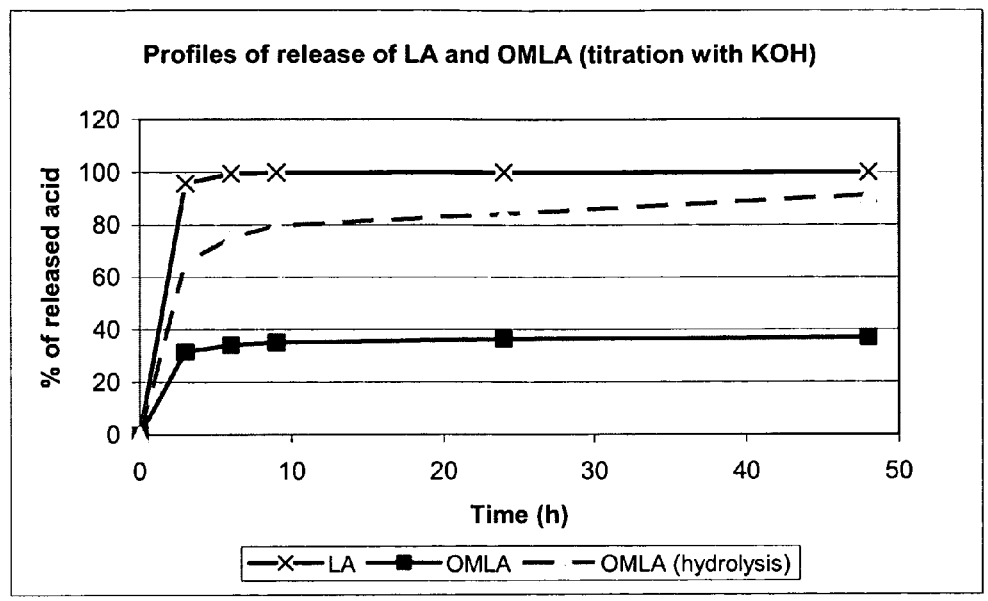
Figure 4:
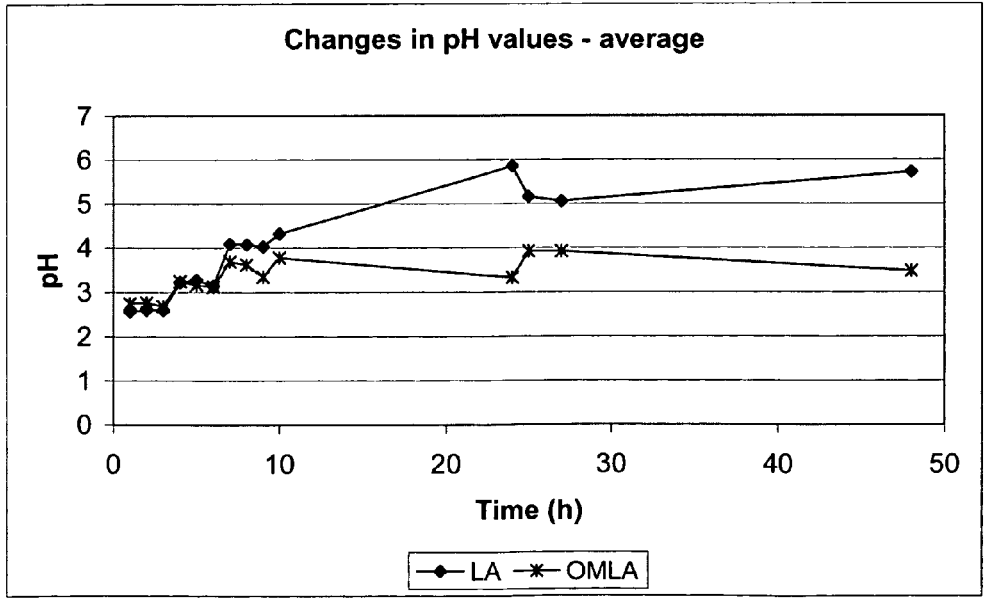

FIG. 4. A) Changes in pH values (average) outside of the dialysis bag: OMLA enables to maintain low pH for longer time than LA. B) Release profiles of LA and OMLA from the dialysis bag: Lactic acid is released from the dialysis bag immediately, while 50% of OMLA (higher molecular weight) is released fast and 50% is released slowly (middle line). OMLA of the higher molecular weight does not hydrolyse in water for a long time, since the middle line is higher than the lowest line (release of acids form OMLA).

Figure 5:
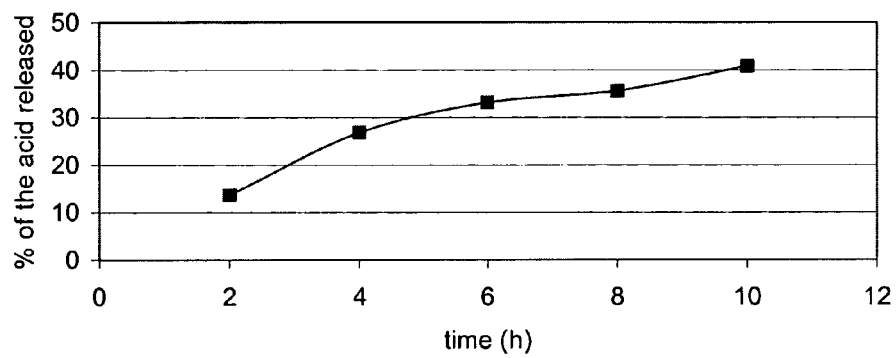
Figure 5:
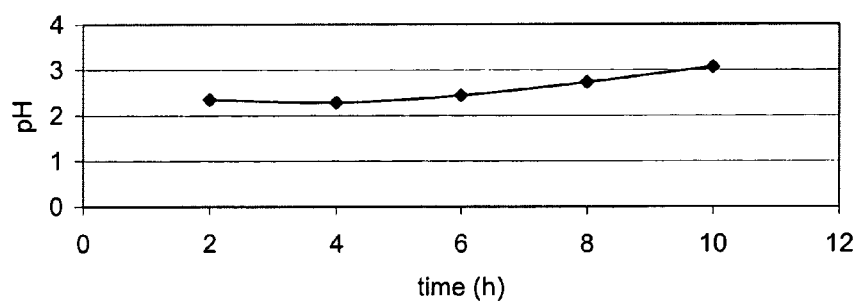

FIG. 5. A) Flow through cell for suppositories at 37° C. B) The changes of the pH of the acceptor water (at 37° C.) as a function of time in Example 4.

Figure 6:
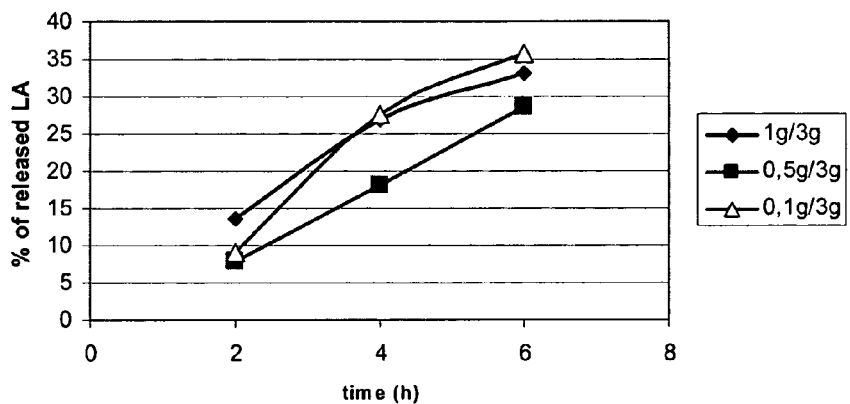
Figure 6:
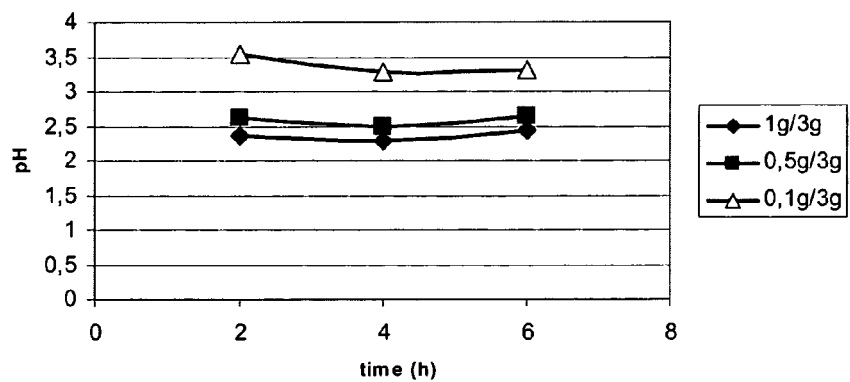

FIG. 6. A) Flow through cell for suppositories at 37° C. The release of acids (% total) from pessaries does not depend on the OMLA-gelatine ratio. B) Flow through cell for suppositories at 37° C. Due to lowest content of OMLA in the pessary 0.1/3 g the decrease of pH is the lowest. Thus the OMLA content in the formulation is a factor which enables pH regulation.

Figure 7:
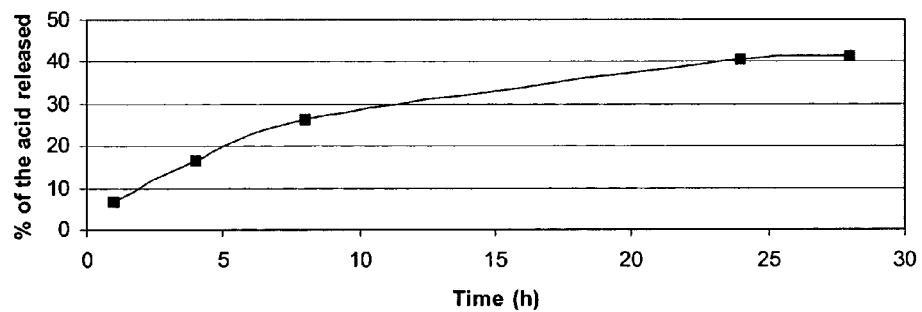
Figure 7:
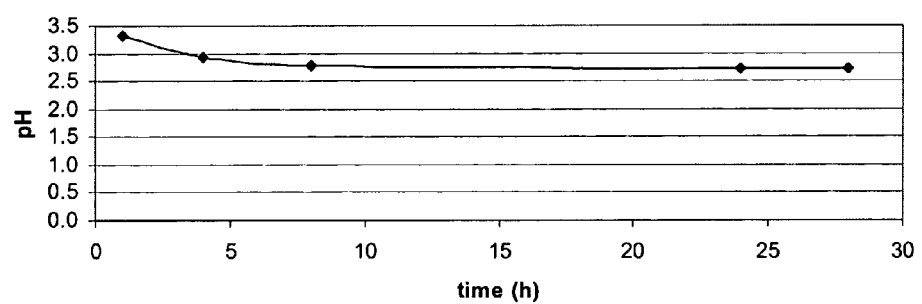

FIG. 7. A) The release of LA from a gel in a dialysis magnetic cell at 37° C. The release of OMLA acids from gel is prolonged and does not show the initial "burst" observed for OMLA (FIG. 3). B) The changes of the pH of the acceptor water (at 37° C.) as a function of time in Example 7, in a dialysis magnetic cell at 37° C. The pH of the acceptor fluid is constant for a long time due to slow release of OMLA acids from the HEC gel.

Figure 8:
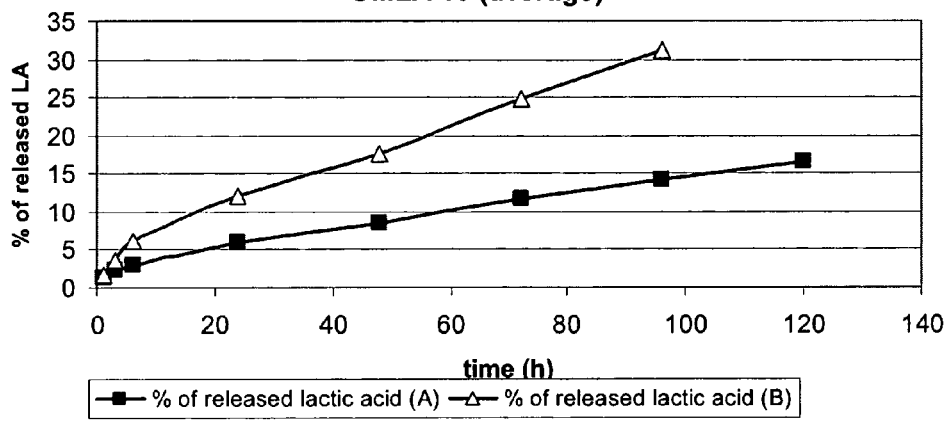
Figure 8:
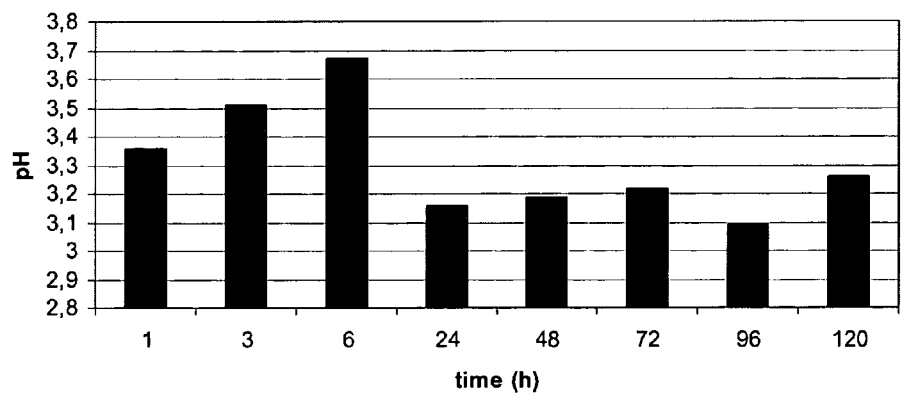

FIG. 8. A) Flask with magnetic stirrer at 37° C. The lower line presents the release of OMLA acids from the EC disc, while the upper shows that part of the OMLA released form the disc is still non degraded and release acids only after full hydrolysis. B) Flask with magnetic stirrer at 37° C. Slow release of OMLA and OMLA acids from the disc results in a reduction of pH for a very long time, despite of the frequent change of the acceptor media to pure water.

Figure 9A:
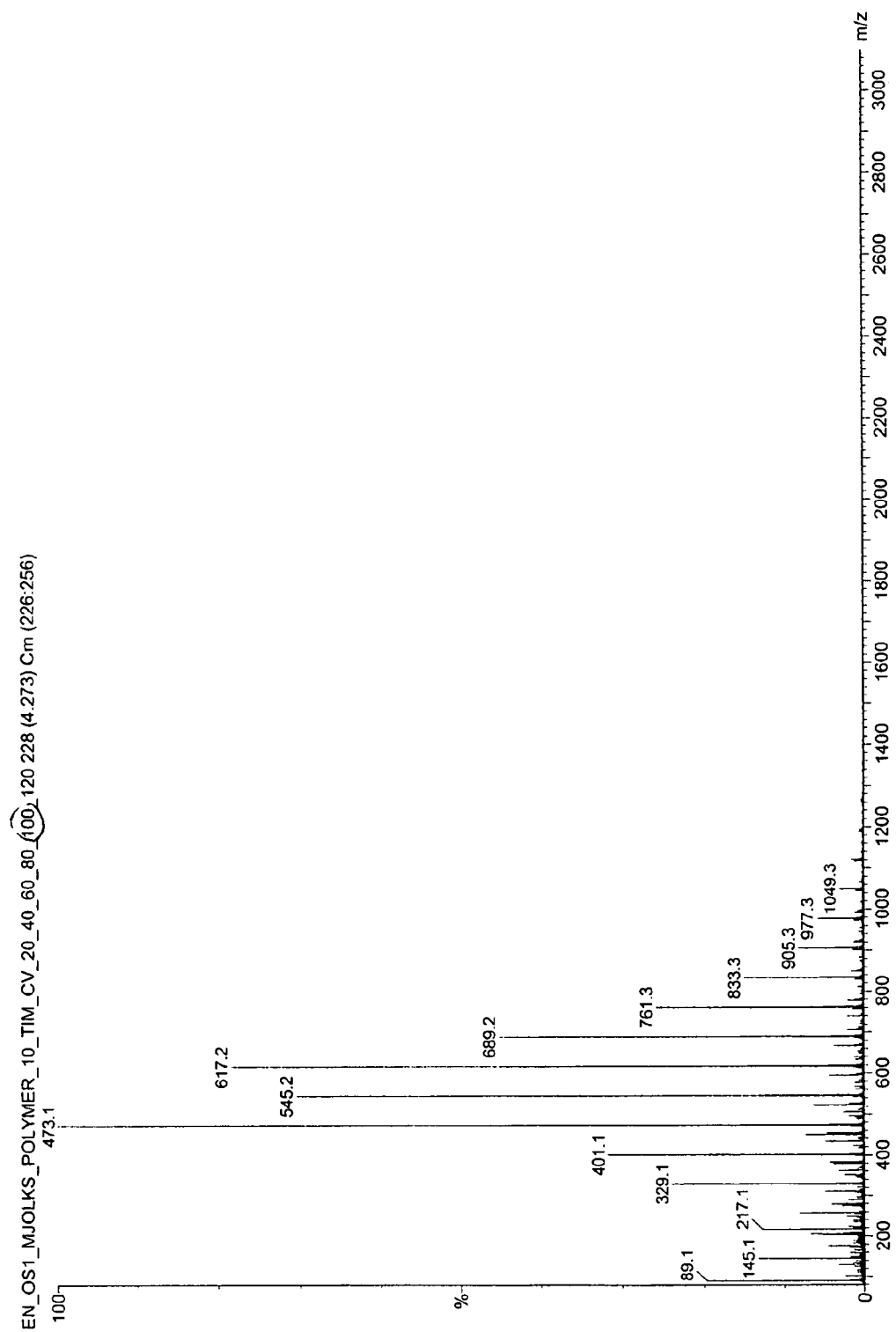
Figure 9B:
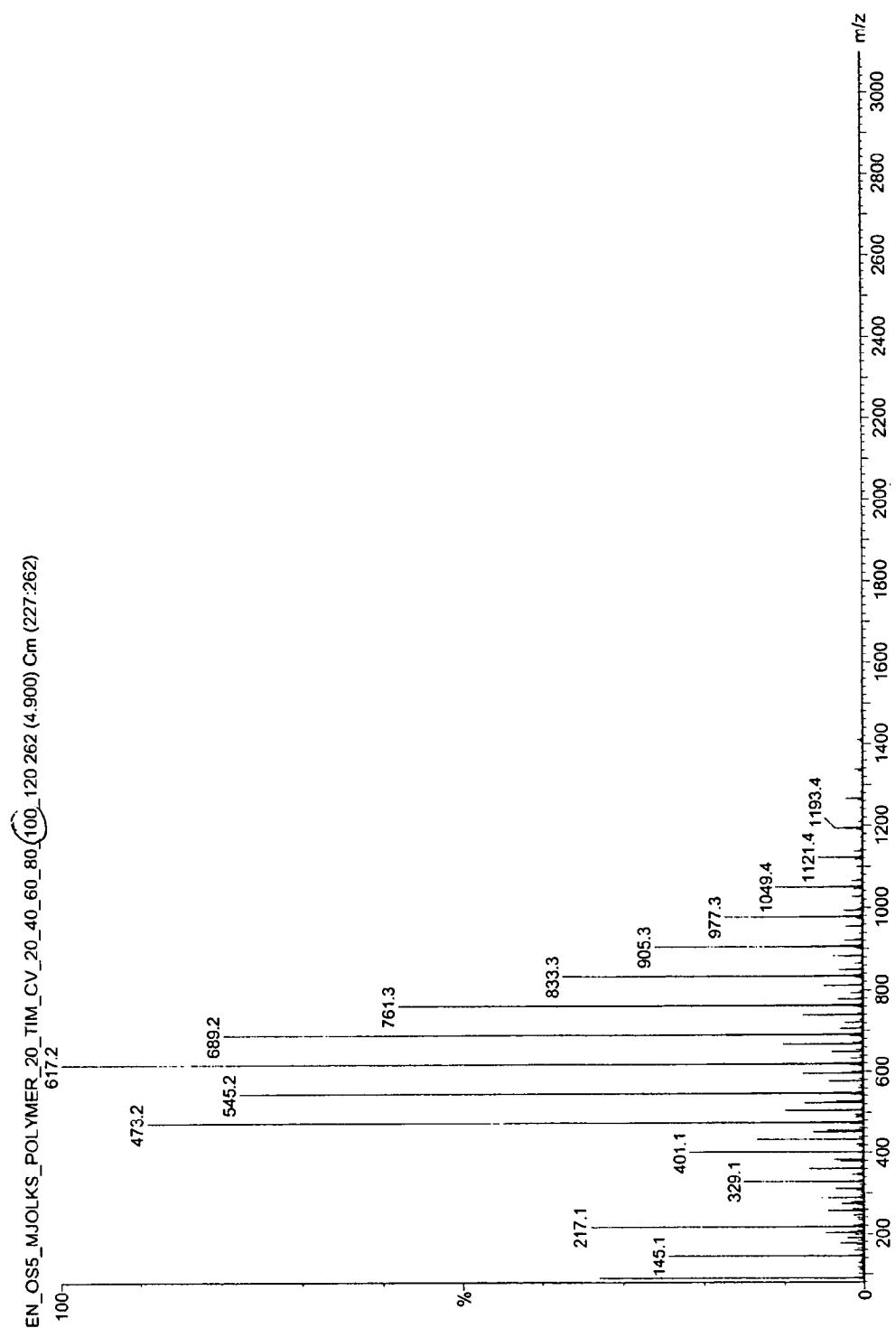
Figure 9C:
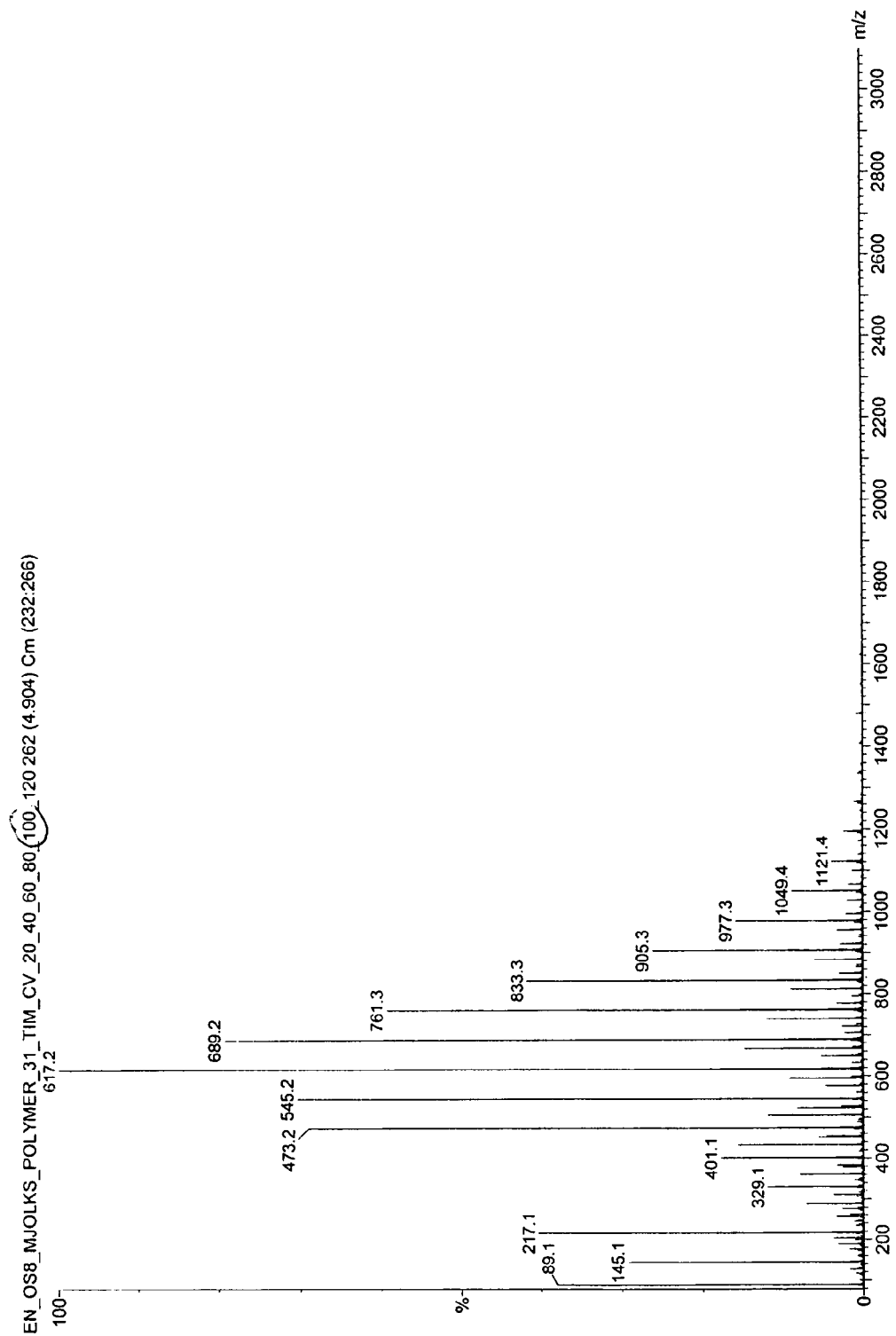

FIG. 9. ESI mass analysis of oligomers of LA produced by heating to 120° C. for A) 10, B) 20, and C) 31 hours, respectively.

Figure 10:
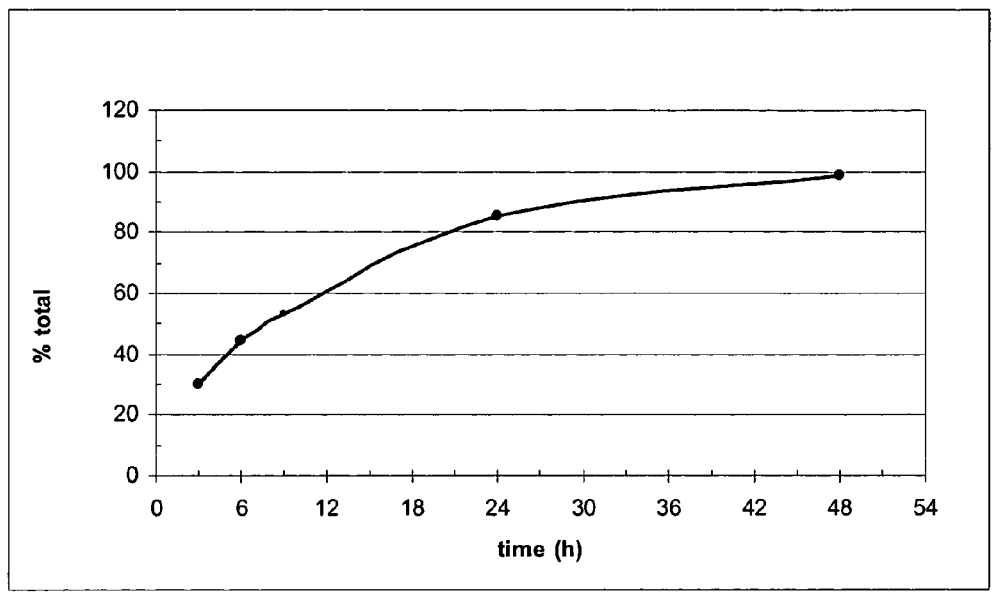

FIG. 10 Lactic acid release via hydrolysis of OMLA 30. The acid release depicted in percentage of total acidic content of OMLA 30. Titration performed with KOH. The acid releasing effect can be seen up to 48 h.

Figure 11:
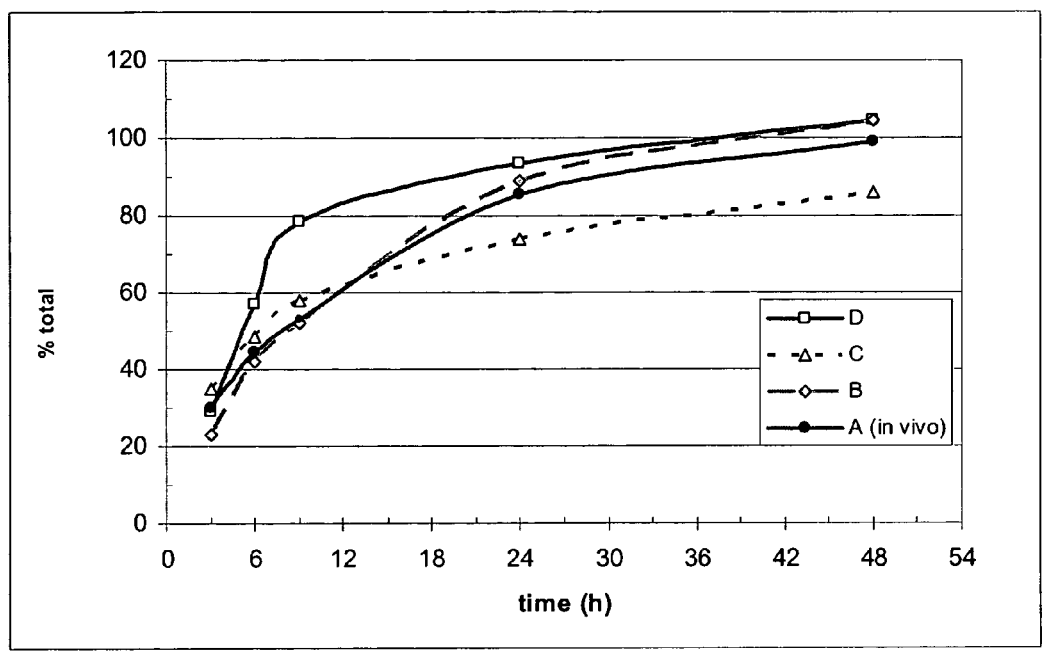

FIG. 11. Four different formulations of lyophilised tablets containing, respectively, different mucoadhesive polymers; A (HMPC (a), tested in vivo), B (HMPC+MC (b)), C (HMPC+MC (c)) and D (HEC (d)), the polymer amount given in Example 15 for each formulation. Acid release is given as percentage of total acid content of OMLA 30 titrated against KOH.

Figure 12A:
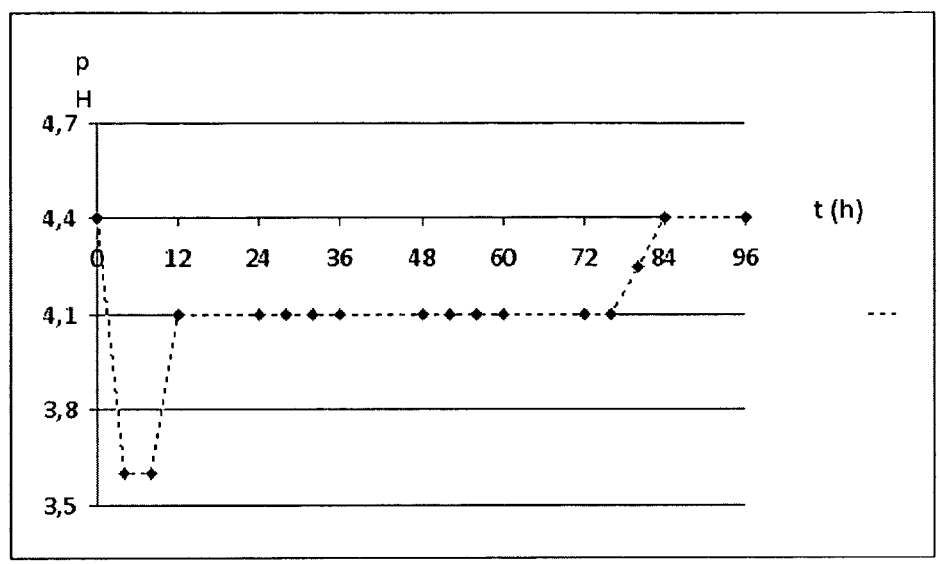

FIG. 12A. The monitoring of administration of OMLA 30 in pessary formulation, displaying both an immediate effect as well as a prolonged effect on the pH in the vaginal tract.

Figure 12B:
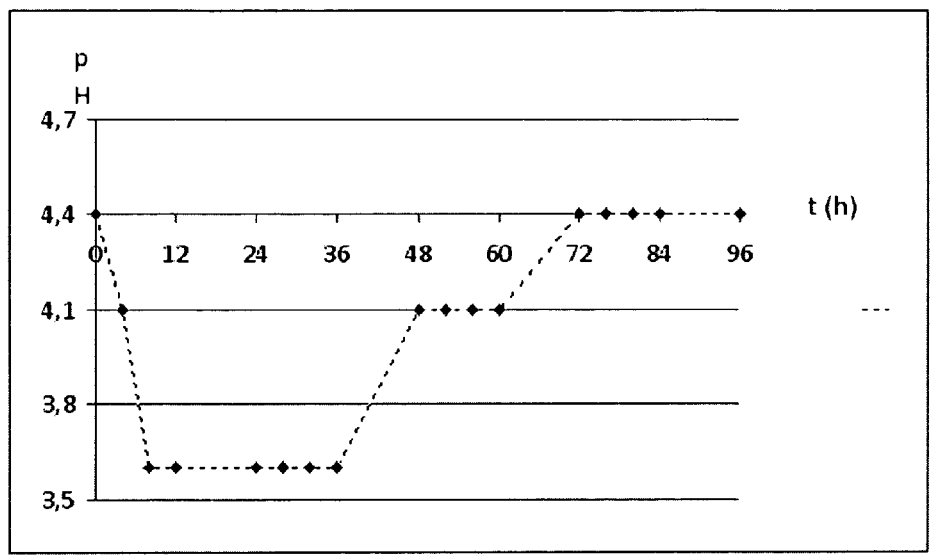

FIG. 12B. The monitoring of administration of OMLA 30 in lyophilized vaginal tablet formulation, displaying a somewhat slower effect on lowering the pH and a total duration 72 h.

Figure 12C:
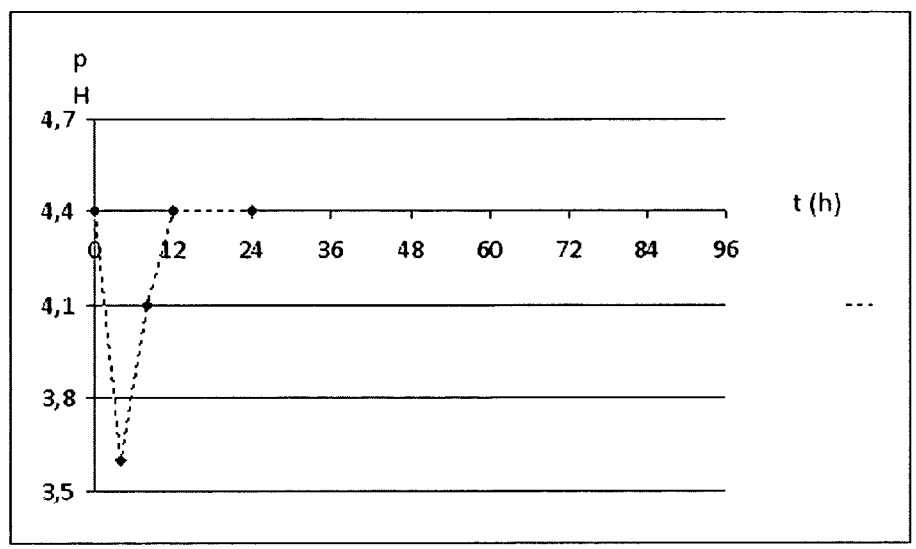

FIG. 12C. The monitoring of administration of Lactal® gel displaying an immediate effect on the pH but no tendency of any persistent effect on keeping a low pH.

Figure 12D:
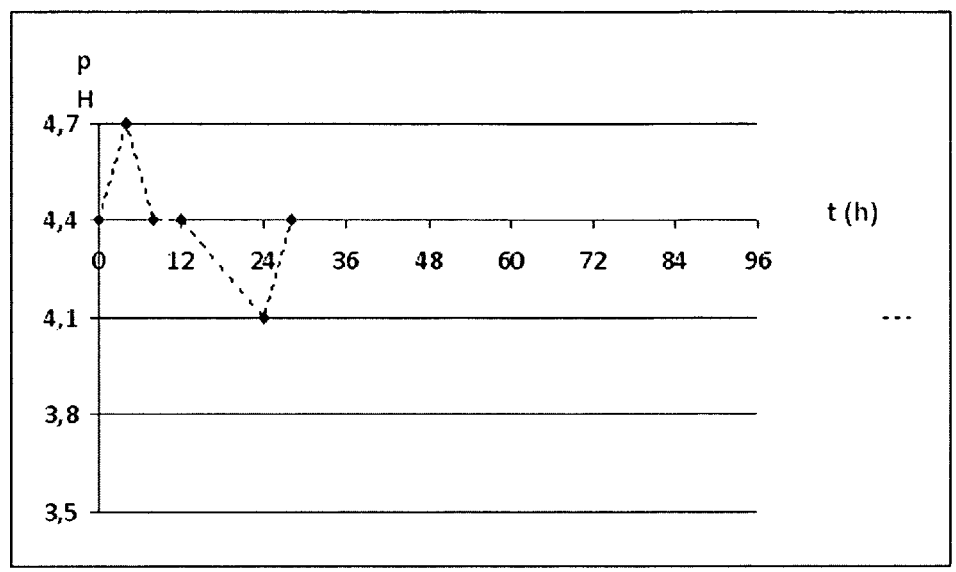

FIG. 12D. The monitoring of administration of Vivag® initially increasing the pH and thereafter lower the same. The lowering effect appears to be present under a period of little more than 12 h.

EXAMPLES

Example 1

Preparation of an Oligomer of Lactic Acid

Oligomers of lactic acid (OMLA) were produced by heating a commercial quality of lactic acid (LA), containing 85% LA and 15% water, at 120° C. in open tubes for different times, thus oligomerising LA to various degrees and producing products with varying viscosity. The number of the OMLA product (e.g. OMLA 12) indicates for how many hours it was heated.

The various oligomers were characterised as described in Example 9.

Example 2

In Vitro Release of Lactic Acid from OMLA 12

This experiment demonstrates the efficiency of OMLA as a source of acidic components and for retaining low pH for a prolonged time.

Release of acidity from OMLA (OMLA 12, formed after 12 hours at 120° C.). OMLA 12, 1 g, was placed in a dialysis bag which was placed in distilled water, 50 ml, at room temperature. The water was stirred continuously with a magnet stirrer. The pH of the water was measured at regular intervals, after replacing the liquid as well as during the intervals between exchanges. After 3, 7 and 47 hours the water was exchanged with fresh water. The results are shown in FIG. 1, where the graphs demonstrate the changes of pH measured in water outside the dialysis bag. FIG. 1A represents the pH value 1 h after replacing the liquid, and FIG. 1B-1D show pH change through the periods between the exchanges of water outside of the dialysis bag. It is evident that OMLA produces acid for many hours (days) during the experimental conditions.

The results indicate that the release of acidic components from OMLA is constant and prolonged.

Example 3

In Vitro Release of Lactic Acid from OMLA 31

This experiment demonstrates the efficiency of OMLA as a source of acidic components and for retaining low pH for a prolonged time and allows for comparison whether the effect can be related to the molecular weight of OMLA.

An experiment identical to Example 2 was conducted with OMLA 31 (formed after 31 hours at 120° C.), although the water outside of the dialysis sac was exchanged more frequently (every hour up 7 h, and later after 21, 45 and 88 h). Results are shown in FIG. 2. FIG. 2A represents the pH value 1 h after replacing the liquid, and FIG. 2B-2D show pH change through the periods between the exchanges of water outside of the dialysis bag.

The conclusions are the same as given in Example 2. Moreover, it is demonstrated that depending on the molecular weight of OMLA the reduction of pH may be larger or smaller: pH between 3 and 4.5 was easier to maintain when OMLA 31 was used, while with OMLA 12 the pH was below 3.0 for long time intervals.

Example 4

Titration of Free Carboxylic Groups in OMLA

The experiment demonstrates acidity of OMLA as a content of carboxylic groups and evaluates the rate of OMLA hydrolysis to free LA.

209 mg of OMLA 31 was suspended in pure water at 20° C. and the solution was titrated with KOH (0.01 M) until a neutral solution was obtained (as verified with a pH indicator). The amount of KOH needed to neutralise the solution at time zero was equivalent to approximately 100 mg LA. At regular intervals, when the spontaneous production of LA had lowered the pH, more KOH was added to maintain the solution neutral. The results are shown in FIG. 3, and demonstrate that there is a rather constant production of LA equivalents from OMLA 31 over time, a few mg per hour during neutral conditions. (All OMLA 31 is expected to be hydrolysed when approximately 230-240 mg LA has been accounted for.)

The results demonstrate that the degradation of OMLA to free LA is slow, but the initially acidic environment is produced due to carboxylic free groups of OMLA.

Example 5

Comparison of In Vitro Release of Lactic Acid from Lactic Acid and OMLA 30, Respectively, Through a Dialysis Membrane The experiment demonstrates the difference between LA and OMLA in respect of the ability to maintain constant acidic pH and proves that hydrolysis of OMLA to LA is slow. 200 mg of LA or OMLA was placed in a dialysis bags. The bags were immersed in 50 ml of water (37° C.) and stirred in the same temperature for 48 hours. After 3, 6, 24 and 48 hours the acceptor liquid was removed and replaced with fresh water. The pH was measured at regular intervals. The liquid was titrated with 0.1 or 0.01 M KOH to measure how much LA equivalents are released. Then an excess of KOH was added and after 24 hours the solution was titrated with 0.1 or 0.01 HCl. This was to evaluate how much of the polymer was dissolved, but did not undergo hydrolysis. The results are presented in FIG. 4A. pH was measured outside of the dialysis bags each hour between 1 to 10 and periodically up to 48 hours (FIG. 4B).

LA is released from the dialysis bag immediately, while 50% OMLA (portion with lower molecular weight and free LA) is released fast and OMLA is slowly released. The portion of OMLA which diffuses through the dialysis membrane but does not release LA can be measured after total hydrolysis with KOH (middle line, FIG. 4A). If OMLA is placed in the dialysis bag, slow release of the acidic components allows for maintaining constant acidic pH for a long time despite of the frequent change of water outside of the dialysis membrane. LA itself is not able to maintain acidic pH constant since it is all present in the acceptor media after short time and is removed while the acceptor fluid is exchanged. This proves that OMLA is suitable for maintaining constant acidic environment and this effect is not possible when LA is used.

Example 6

In Vitro Release of Lactic Acid from a Formulation Containing OMLA 16

| Preparation of pessaries | [g] |
|---|---|
| OMLA 16 | 1.0 |
| Gelatin | 0.35 |
| Water | 0.3 |
| Glycerine | 1.35 |

OMLA was mixed together with a part of the glycerine. The rest of substances were mixed and heated until the gelatine dissolved and added to the mixture of glycerine and OMLA. After homogenisation, the mixture was poured into pessary forms and refrigerated.

The pessaries (2.5 g) were placed in the Ph. Eur. flow-through apparatus for dissolution testing of suppositories and the release test was performed. The acceptor was water (37° C., the flow rate was 12.5 ml/h). After 2, 4, 6, 8 and 10 h the liquid was collected and the content of LA and pH was measured. The release profile of LA as well as the pH of the water is shown in FIGS. 5A and 5B. Despite of the fast disintegration and dissolution of gelatin from the pessaries the release of acid continues for a long time. The release of acids results in low pH for a long time, despite of the fact that all time a fresh water is flowing through the chamber—LA itself would have be completely removed for this time.

Another experiment was conducted as described above with different amounts of OMLA in the pessaries, from 33% (as in Example 4) via 16.5% to 3.3%. The results are shown in FIG. 6. The release of acids (% total) from pessaries does not depend on the OMLA-gelatin ratio, although due to lowest content of OMLA in the pessary 0.1/3 g the reduction of pH is the smallest. Thus OMLA content in the formulation is a factor which enables pH regulation.

The gelatin-based pessary is an appropriate formulation which enables prolonged release of LA and reduction of the environment pH in a manner depending on the OMLA-pessary base ratio.

Example 7

In Vitro Release of Lactic Acid from OMLA 20 in a Gel Formulation

| Preparation of gel: | [g] |
|---|---|
| OMLA 20 | 1.0 |
| Hydroxyethyl cellulose (Natrosol 250) | 0.25 |
| Glycerol | 1.5 |
| Ethanol 95% v/v | 2.0 |
| Water | ad 10.0 |

OMLA was dissolved in mixture of ethanol and glycerine. Hydroxyethyl cellulose was suspended in water and added to the solution of OMLA while stirring intensively. Then the mixture was heated to 50° C. and continuously stirred until the gel was formed.

1 g of the gel (10% OMLA) was placed in a dialysis magnetic chamber and stirred in 50 ml water at 37° C. After 1, 4, 8, 24 and 28 hours, 20 ml of the acceptor fluid was replaced by fresh water (37° C.). pH of the samples was measured and 10 ml of the sample was titrated with 0.01 M KOH and from this the amount of the LA was calculated. The results are shown in FIG. 7.

The release of OMLA acids from the gel is prolonged and does not show the initial "burst" like it was observed for OMLA substance (FIG. 3), what results from the slow release of OMLA from the gel matrix. As a consequence the pH of the acceptor fluid is constant for a long time.

Example 8

In Vitro Release of Lactic Acid from OMLA 10 in a Disc Formulation

This experiment demonstrates whether OMLA can be incorporated into a solid non-degradable formulation which can release acidic components and maintain reduced pH of the environment.

Preparation of the Disc:

0.5 g of OMLA 10 and 2.5 g of ethylcellulose were dissolved together in methylene chloride. The mixture was placed in a Petri dish where the solvent was allowed to evaporate and the disc was formed.

Release Test:

The disc was cut in two parts and both of them were placed in separate flasks filled with 50 ml of water (37° C.). The contents of the flasks were stirred at 37° C. and after 1, 3, 6, 24, 48, 72 and 96 h the liquid was removed and replaced with fresh water.

25 ml of the collected liquid was titrated with 0.01 M KOH. In order to evaluate the amount of the acidic components that was released but did not hydrolyse, the excess of the base was added and after few hours the mixture was titrated with 0.01 M HC1. FIG. 8A presents the results of the release test without (sample A) and with the step of additional hydrolysis (sample B).

pH was measured in the rest of the liquid. FIG. 8B presents the changes in pH value with the progress of the experiment.

FIG. 8A demonstrates that the release of acidic components from the ethylcellulose disc is slow and can be maintained for a long time (days). After 5 days only 15-20% of LA was released. This maintains constant acidic pH of the acceptor fluid, despite of partial exchange into fresh water. OMLA is also released, what is presented after total hydrolysis to LA (sample B). After 4 days nearly 70% of OMLA still resides in the disc. Changing composition of the matrix different rates of the drug release from the disc can be achieved.

Example 9

Mass Analysis of Oligomers of LA Produced by Heating to 120° C. for 10, 20, and 31 Hours, Respectively.

ESI mass analysis of oligomers of LA, produced simply by heating LA to 120° C. at different times. The products were prepared by heating of LA to 120° C. for 10 (FIG. 9A), 20 (FIG. 9B), and 31 (FIG. 9C) hours.

The peaks correspond to: 145:cyclic dimer and $H^+$, 257: trimer and $Na^+$, 329:tetramer and $Na^+$, 401:pentamer and $Na^+$, 473:hexamer and $Na^+$, 545:heptamer and $Na^+$, 617: octamer and $Na^+$, 689:nonamer and $Na^+$, 761:decamer and $Na^+$, 833:undecamer and $Na^+$, 905:dodecamer and $Na^+$, 977: tridecamer and $Na^+$, 1049:tetradecamer and $Na^+$, 1121:pentadecamer and $Na^+$, 1193:hexadecamer and $Na^+$, 1265:heptadecamer and $Na^+$, etc.

The "Gauss distribution" slowly shifts to higher molecular weights with time of heating. Other parameters besides time, e.g. temperature, water content, pressure, catalyst etc. will influence the result. By mixing oligomeric products obtained in different ways it is possible to prepare oligomeric mixtures with any composition.

Example 10

Mucoadhesive Properties of OMLA Formulations

Chemical and preformulation experiments were carried out in order to determine mucoadhesiveness of OMLA in gel or semisolid forms (see table below). The mucoadhesiveness for the OMLA judged for fluid, gel, patch, and vagitoria. Muco(Bio)adhesiveness is given according to a 5 graded VAS scale, where 0 denotes no mucoadhesive properties and 4 very pronounced mucoadhesive properties.

Mucoadhesive Properties of OMLA Formulations

| | Fluid | Gel | Patch | Vagitoria |
|---|---|---|---|---|
| Lactic acid, 85% purity | 0 | — | — | — |
| OMLA (mainly tetramer to octamer) | — | 3 | 4 | 3 |
| OMLA (mainly pentamer to decamer) | — | 4 | 4 | 4 |

Lactate containing 15% water is a liquid and present only in fluid form, while the OMLA product becomes more and more viscous when extending the length of the molecule.

Example 11

Synthesis of Oligomers of Lactic Acid (OMLA)

Composition of Starting Material

L-Lactic acid was used as starting material. The composition of the starting material in aqueous solution at 25° C. at equilibrium is as follows:

| TA | HL1 | HL2 | HL3 | HL4 | HL5 | FA | W | P |
|---|---|---|---|---|---|---|---|---|
| 90 | 65.51 | 17.33 | 3.68 | 0.71 | 0.13 | 76.79 | 12.64 | 1.172 |

Property: Composition of Lactic Acids and its Oligomers in Equilibrium at 25° C.
TA: Total Concentration Lactic Acid, % w/w
HL1: Concentration Monomeric Lactic Acid, % w/w
HL2: Concentration Lactoyl Lactic Acid, % w/w, MW = 162
HL3: Concentration Lactoyllactoyl Lactic Acid, % w/w, MW = 234
HL4: MW = 306
HL5: MW = 378
FA: Direct titratable acidity calculated as lactic acid
W: Percentage Water, % w/w
P: Degree of Polymerization (=TA/FA)
Note:
Concentrations of the oligomers are not expressed as lactic acid, but as relative to the component.

Two series of synthesis were performed. In the first series (001/1-5) the synthesis was performed by heating the above-mentioned starting material containing 10% w/w of water at 120° C. for 18 h (001/1), 24 h (001/2), 31 h (001/3), 41 h (001/4) and 51 h (001/5). In the second series (002/1-5), the synthesis was performed by heating the above-mentioned starting material containing 10% w/w of water at 140° C. for 18 h (002/1), 24 h (002/2), 31 h (002/3), 41 h (002/4) and 51 h (002/5). The heating is performed in open vessels allowing the water content to evaporate.

The compositions of the products obtained were evaluated by HPLC analysis.

Oligomer Determination:

The lactic acid, lactide, meso-lactide and the lactic acid oligomers are separated using liquid chromatography and quantified with UV detection. The actual separation of the oligomers is performed with a gradient system in which the concentration of the organic solvent is increased during the run. The UV response of the oligomers is measured at a wavelength at which carbonyl-and ester-bonds are known to adsorb. The quantification is done using an external standard method.

Free Acid Determination:

The free acid was determined using a solvotrode and a non-aqueous titration. A mixture of methanol and dichloromethane was used to dissolve the samples. The titration was done using potassium methanolate as a titrant.

Moreover, it was noted that both L-and D-lactide was present, i.e. the synthesis does not seem to be stereoselective and, accordingly, it is envisaged that both L-lactic acid oligomers, D-lactic acid oligomers as well as mixtures therof including racemic mixtures are present.

Composition of Products

| Sample code/name | Description |
|---|---|
| 1 | Lac2008.001/1 |
| 2 | Lac2008.001/2 |
| 3 | Lac2008.001/3 |
| 4 | Lac2008.001/4 |
| 5 | Lac2008.001/5 |
| 6 | Lac2008.002/1 |
| 7 | Lac2008.002/2 |
| 8 | Lac2008.002/3 |
| 9 | Lac2008.002/4 |
| 10 | Lac2008.002/5 |

TABLE 1

HPLC lactide and oligomers of lactic acid for samples Lac2008.001/1-5:

| component | | 1 | 2 | 3 | 4 | 5 |
|---|---|---|---|---|---|---|
| meso-lactide | [% (w/w)] | <0.1 | <0.1 | <0.1 | <0.1 | <0.1 |
| D + L lactide | [% (w/w)] | 1.1 | 1.2 | 1.2 | 1.5 | 1.4 |
| HL | [% (w/w)] | 10.5 | 7.2 | 6.1 | 4.2 | 3.2 |
| $HL_2$ | [% (w/w)] | 17.2 | 12.5 | 9.8 | 6.4 | 5.2 |
| $HL_3$ | [% (w/w)] | 19.6 | 15.3 | 12.3 | 9.0 | 7.5 |
| $HL_4$ | [% (w/w)] | 16.0 | 13.9 | 12.2 | 9.9 | 8.3 |
| $HL_5$ | [% (w/w)] | 12.0 | 11.8 | 11.0 | 9.5 | 8.5 |
| $HL_6$ | [% (w/w)] | 8.6 | 9.8 | 9.5 | 8.9 | 8.2 |
| $HL_7$ | [% (w/w)] | 6.3 | 8.5 | 8.4 | 8.7 | 8.4 |
| $HL_8$ | [% (w/w)] | 4.2 | 6.0 | 6.6 | 7.2 | 7.1 |
| $HL_9$ | [% (w/w)] | 2.8 | 5.0 | 5.8 | 6.4 | 6.7 |
| $HL_{10}$ | [% (w/w)] | 1.9 | 3.4 | 4.5 | 5.7 | 6.2 |
| $HL_{11}$ | [% (w/w)] | 1.1 | 2.6 | 3.6 | 4.6 | 5.3 |
| $HL_{12}$ | [% (w/w)] | 0.8 | 1.9 | 2.9 | 4.0 | 4.7 |
| $HL_{13}$ | [% (w/w)] | 0.5 | 1.3 | 2.1 | 3.2 | 4.0 |
| $HL_{14}$ | [% (w/w)] | 0.2 | 1.0 | 1.7 | 2.7 | 3.4 |
| $HL_{15}$ | [% (w/w)] | <0.1 | 0.5 | 1.0 | 1.9 | 2.8 |
| $HL_{16}$ | [% (w/w)] | <0.1 | 0.5 | 0.8 | 1.8 | 2.5 |
| $HL_{17}$ | [% (w/w)] | <0.1 | <0.1 | 0.8 | 1.6 | 2.2 |
| $HL_{18}$ | [% (w/w)] | <0.1 | <0.1 | 0.6 | 1.5 | 1.9 |
| Sum $HL_{1\ t/m\ 18}$ | [% (w/w)] | 102.9 | 102.6 | 101.0 | 98.7 | 97.5 |

HL corresponds to the monomeric lactic acid, $HL_2$ to the dimmer, $HL_3$ to the trimer etc.

TABLE 2

HPLC lactide and oligomers of lactic acid for samples Lac2008.002/1-5:

| component | | 1 | 2 | 3 | 4 | 5 |
|---|---|---|---|---|---|---|
| meso-lactide | [% (w/w)] | <0.1 | <0.1 | <0.1 | <0.1 | <0.1 |
| D + L lactide | [% (w/w)] | 1.7 | 1.7 | 1.8 | 1.9 | 2.0 |
| HL | [% (w/w)] | 5.1 | 3.0 | 2.5 | 1.6 | 0.9 |
| $HL_2$ | [% (w/w)] | 7.7 | 5.6 | 4.1 | 2.7 | 2.0 |
| $HL_3$ | [% (w/w)] | 10.1 | 7.0 | 5.7 | 4.0 | 3.0 |
| $HL_4$ | [% (w/w)] | 10.8 | 8.1 | 6.5 | 4.6 | 3.5 |
| $HL_5$ | [% (w/w)] | 10.3 | 8.2 | 6.8 | 5.0 | 4.2 |
| $HL_6$ | [% (w/w)] | 9.1 | 7.9 | 6.7 | 5.3 | 4.4 |
| $HL_7$ | [% (w/w)] | 8.9 | 8.2 | 7.3 | 5.9 | 5.1 |
| $HL_8$ | [% (w/w)] | 7.2 | 6.7 | 6.3 | 5.3 | 4.9 |
| $HL_9$ | [% (w/w)] | 6.2 | 6.1 | 5.9 | 5.3 | 4.7 |
| $HL_{10}$ | [% (w/w)] | 5.5 | 6.1 | 5.6 | 5.1 | 4.5 |
| $HL_{11}$ | [% (w/w)] | 4.4 | 4.9 | 5.2 | 4.9 | 4.4 |
| $HL_{12}$ | [% (w/w)] | 3.6 | 4.2 | 4.4 | 4.4 | 4.3 |
| $HL_{13}$ | [% (w/w)] | 3.0 | 3.6 | 4.0 | 4.1 | 3.9 |
| $HL_{14}$ | [% (w/w)] | 2.5 | 3.1 | 3.2 | 3.8 | 3.6 |
| $HL_{15}$ | [% (w/w)] | 1.7 | 2.4 | 2.7 | 3.3 | 3.3 |
| $HL_{16}$ | [% (w/w)] | 1.4 | 2.2 | 2.5 | 3.4 | 3.1 |
| $HL_{17}$ | [% (w/w)] | 1.2 | 1.9 | 2.4 | 2.3 | 2.8 |
| $HL_{18}$ | [% (w/w)] | 0.9 | 1.5 | 2.0 | 2.5 | 2.5 |
| Sum $HL_{1\ t/m\ 18}$ | [% (w/w)] | 101.2 | 92.2 | 85.6 | 75.4 | 67.3 |

The overall mass-balance of the last samples is incomplete because there are higher oligomers of lactic acid present in the samples. These are not included in Sum $HL_{1\ t/m\ 18}$.

The above-mentioned results were used to calculate $M_n$ and $M_w$ and the polydispersity index. The following results were obtained.

TABLE 3

Number and weight average molecular weights and polydispersity index for samples 1-10

| | Sample | | | | | | | | | |
|---|---|---|---|---|---|---|---|---|---|---|
| | 1 | 2 | 3 | 4 | 5 | 6 | 7 | 8 | 9 | 10 |
| Mn | 323 | 396 | 472 | 573 | 629 | 571 | 721 | 839 | 1031 | 1138 |
| Mw | 426 | 530 | 661 | 791 | 848 | 726 | 992 | 1198 | 1547 | 1682 |
| Polydispersity index | 1.32 | 1.34 | 1.40 | 1.38 | 1.35 | 1.27 | 1.38 | 1.43 | 1.50 | 1.48 |
| n | 4-6 | 5-8 | 6-9 | 7-11 | 8-12 | 7-10 | 9-14 | 11-17 | 14-22 | 15-24 |

The number n indicates average degree of oligomerisation (i.e. n=4 relates to the tetramer, 5 to the pentamer, 6 to the hexamer etc.).

As seem from the table above, an increase in reaction time as well as an increase in reaction temperature leads to an increase in the average molecular weight. Moreover, the polydispersity index tends to increase with reaction time for the series synthesized with a reaction temperature is 140° C. Moreover, it seems as if the polydispersity index is relatively independent on the reaction time, when a reaction temperature of 120° C. is employed.

Example 12

Stability of OMLA 30 Stability in Water

OMLA 30 was prepared by heating L-lactic acid at 120° C. for 30 hours.

The employment of oligomers of lactic acid as depot forms of lactic acid is dependent on their ability to hydrolyse into lactic acid (or smaller oligomers) in order to maintain or an acid pH (or decrease pH) in the environment.

Three samples of OMLA 30 (1.0 g each) were placed in separate vials. One of them was mixed with 0.1 g of water (sample B), another one with 0.5 g of water (sample C) and one was water-free (sample A). All vials were stored for 1 week at 60° C. Within this time the samples containing water (B and C) underwent dissolution and less viscous solution developed. As a control sample A was also stored at 4° C. (a control).

After 7 days the samples from each vial were titrated with 0.1 M KOH. The volume of the used KOH is given in the Table (volume P).

Than an excess of KOH was added to each flask and after two days of stirring the samples were considered as totally hydrolysed. The access of KOH was titrated with 0.1 M HCl. From this titration the amount of KOH reacting with LA produced form the totally hydrolysed sample was calculated. The volume of KOH reacting with LA from totally hydrolysed OMLA was considered as 100% (volume T).

$F = (\text{volume } P \times 100\%)/\text{volume } T$ only when F is 100% all titrated carboxylic groups are from LA, otherwise free carboxylic groups of OMLA contribute to the F value.

| Sample | Storage (7 days) | Mass of sample titrated [mg] | Volume of KOH [ml] | F % of free carboxylic groups | F average (%) | Appearance |
|---|---|---|---|---|---|---|
| A without water | 60° C. | 236 | 4.85 | 14.83 | 13.0 | Semisolid |
| | | 191 | 3.1 | 11.23 | | Semisolid |
| B 10% water | 60° C. | 283 | 18.3 | 50.8 | 50.0 | Dissolved |
| | | 198 | 12.4 | 49.2 | | Dissolved |
| C | 60° C. | 395 | 30.8 | 85.3 | 85.7 | Dissolved |

-continued

| Sample | Storage (7 days) | Mass of sample titrated [mg] | Volume of KOH [ml] | F % of free carboxylic groups | F average (%) | Appearance |
|---|---|---|---|---|---|---|
| 33% of water | | 374 | 29.35 | 86.07 | | Dissolved |
| A without water | 4° C. | 253 | 2.85 | 8.52 | 8.2 | Semisolid |
| | | 224 | 2.4 | 7.97 | | semisolid |

From the results given above, it is seem that the oligomeric product is relatively stable if water is not present and the rate of hydrolysis increases with increase of the water concentration. Accordingly, it is expected that suitably stable pharmaceutical compositions containing the oligomeric products can be obtained and that such compositions after application e.g. to vagina releases lactic acid in a prolonged manner, which in turn can lead to a prolonged effect, i.e. a prolonged maintenance of an acid pH value in the vagina.

Example 13

Pharmaceutical Compositions Containing OMLA—Lyophilized Tablets

A tablet-like formulation was prepared by subjecting a gel to lyophilization in a blister package as described in the following.

The lyophilized tablets were used in a pilot in vivo study (see Example 17)

Gel Subjected to Lyophilization [g]:

| OMLA 30 | 20 |
|---|---|
| lactose | 10 |
| Pharmacoat* 6 cP | 20 |
| water | 50 |

*hypromellose USP (Shin-Etsu Chemical)

Preparation:

Lactose was dissolved in water and hypromellose was added gradually with an intensive stirring. When the polymer dissolved, to the resulting gel OMLA was added and the gel was mixed thoroughly.

The OMLA containing gel was dispensed to the blister wells (2 g per well) and freeze dried. The following "tablets" were obtained:

Lyophilized Tablet (A) [mg]:

| OMLA 30 | 400 |
|---|---|
| lactose | 200 |
| hypromellose | 400 |

Freeze Drying:

The following operating conditions were applied during the process:

| Pressure: | 0-2 h - atmospheric |
|           | 2-48 h - 1 mbar |

Temperature:

| Time (h) | °C. |
|---|---|
| 0-2 | −40 |
| 2-17 | −25 |
| 17-27 | −10 |
| 27-42 | 0 |
| 42-44 | 10 |
| 44-46 | 20 |
| 46-48 | 20 |

Variations

|  | Quality | Quantity |
|---|---|---|
| I. Gel composition | | |
| OMLA 30 -- 20.0 (%) | OMLA 10-30, OMLA Lac2008.003; 007; 007; (+LA) | 2-30% |
| Lactose -- 10% | other sugars and sugar alcohols | 0-50% |
| Pharmacoat 6 cP - 20% | other types of hypromellose, hydroxyethylcellulose, sodium carmellose, methylcellulose, other gellifying and mucoadhesive agents # | 0-40% |
| Water - 50% | with dissolved acids or antimicrobial agents | 15-90% |
| II. Lyophilized tablet | | |
| Cylinder Size: diameter-1 cm height - 1 cm | any shape suitable for vaginal application | |
| OMLA 30 - 400 mg/tabl | as for the gel | 50-1000 mg |
| Lactose - 200 mg | " | |
| Hypromellose | " | |
| III. Gel preparation | | |
| Lactose was dissolved in water and hypromellose was added gradually with an intensive stirring. | Lactose can be added to the ready hypromellose gel. | |
| When the polymer dissolved, to the resulting gel OMLA was added and the gel was mixed thoroughly. | The dispersion of OMLA in the gel may be performed at higher temperature (up to 80° C.). | |
| The OMLA containing gel was dispensed to the blister wells (2 g per well) and freeze dried. | Lyophilization may be performed in other unit dose forms or on trays. In the latter case the discs (cylinders) are cut out from the lyophilized sheet. | |
| IV. Lyophilization | | |
| Time - 48 h | 24-60 h | |
| Temperature (−40° C. to 30° C.) | Freezing may be performed at lower temperature (e.g. −20° C.). The highest temp.: 10-50° C. | |
| Pressure | Up to 20 mbar | |
| Time-temperature | different plan may be suitable | | as already listed herein

Example 14

In Vitro Release of Lactic Acid from Lyophilized Tablets

The lyophilized tablets, A, described in Example 13 and containing OMLA 30 were tested with respect to release of lactic acid. The experiment was performed by placing ½ tablet in a dialysis bag (37° C.) as described in Example 2 herein. The following results were obtained.

Release of acids from OMLA 30 lyophilized tablet (dialysis bag method - 50 ml of the fluid) 14.03.2008.

pH measurements

| lyophilized tablet | pH | | | | | | | | | |
|---|---|---|---|---|---|---|---|---|---|---|
| | 1.5 | 3.0 | 4.5 | 6.0 | 7.5 | 9.0 | 22.5 | 24.0 | 46.5 | 48.0 |
| 20% Pharmacoat 6 cP | 3.03 | 2.92 | 3.23 | 3.15 | 3.52 | 3.30 | 3.16 | 3.11 | 3.35 | 3.27 |

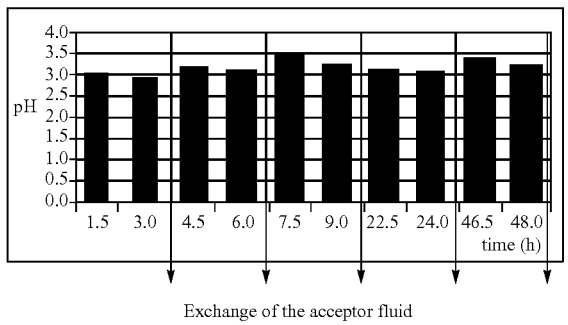

Exchange of the acceptor fluid titration with KOH (acids calculated as lactic acid - % total)

| | acids released (%) | | | | | |
|---|---|---|---|---|---|---|
| 20% Pharmacoat 6 cP | 3 | 6 | 9 | 24 | 48 | time (h) |
| 20% Pharmacoat 6 cP | 29.99 | 44.31 | 52.87 | 85.49 | 98.90 | |

The results are shown in FIG. 10. The results show that it is possible to maintain a low pH for a time period of at least 48 hours. The pH measurements and the determination of acid released (i.e. using titration with KOH) are in agreement.

Example 15

In Vitro Release of Lactic Acid from Lyophilized Tablets Containing Different Types of Mucoadhesive Polymers In the following table are described the composition of lyophilized tablets (and the gels subjected to lyophilization). The tablets contain a mucoadhesive polymers, which improve the adherence of the tablets to the mucosa (e.g. the vaginal mucosa) upon administration

| | A* (in vivo) | B | C | D |
|---|---|---|---|---|
| | Gel for lyophilization (g) | | | |
| OMLA 30 | 20 | 20 | 20 | 20 |
| lactose | 10 | 10 | 10 | 10 |
| mucoadhesive polymer: | | | | |
| type | HPMC (a) | HPMC + MC (b) | HPMC + MC (c) | HEC (d) |
| amount | 20 | 10 | 5 | 15 |
| water | to 100 | to 100 | to 100 | to 100 |
| | Lyophilized tablet (mg) | | | |
| OMLA 30 | 400 | 400 | 400 | 400 |
| lactose | 200 | 200 | 200 | 200 |
| mucoadhesive polymer | 400 | 200 | 100 | 300 |
| total mass(mg) | 1000 | 800 | 700 | 900 |

*the preparation used in vivo; the results presented in details above (see example 14)
HPMC (a)
hypromellose - Pharmacoat 606 - 6 cP (Shin-Etsu Chemical)
HPMC + MC (b)
hypromellose and methylcellulose - Metolose 60SH - 50 cP (Shin-Etsu Chemical)
HPMC + MC (c)
hypromellose and methylcellulose - Metolose 65SH - 4000 cP (Shin-Etsu Chemical)
HEC (d)
hydroxyethylcellulose - Natrosol L - 76 cP (Aqualon)

Release of acids from the lyophilizates was studied as described above in Example 14 for Pharmacoat 606 lyophilized tablet.

pH meaurements

| Formulation | pH | | | | | | | | | | - time h |
|---|---|---|---|---|---|---|---|---|---|---|---|
| | 1.5 | 3.0 | 4.5 | 6.0 | 7.5 | 9.0 | 22.5 | 24.0 | 46.5 | 48.0 | |
| A (in vivo) | 3.03 | 2.92 | 3.23 | 3.15 | 3.52 | 3.30 | 3.16 | 3.11 | 3.35 | 3.27 | |
| B | 3.12 | 2.96 | 3.23 | 3.06 | 3.27 | 3.19 | 2.99 | 3.05 | 3.12 | 3.14 | |
| C | 2.91 | 2.78 | 3.15 | 3.09 | 3.49 | 3.28 | 3.09 | 3.11 | 3.32 | 3.30 | |
| D | 3.01 | 2.95 | 3.05 | 2.96 | 3.34 | 3.29 | 3.29 | 3.33 | 3.48 | 3.41 | |

-continued

The results from compositions A-D are shown from left to right in each block

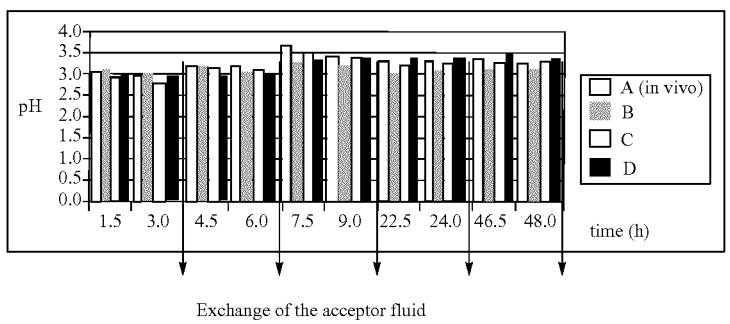

Exchange of the acceptor fluid

| | titration with KOH (acids calculated as lactic acid - % total) | | | | | |
|---|---|---|---|---|---|---|
| | acids released (%) | | | | | |
| Formulation | 3 | 6 | 9 | 24 | 48 | - time h |
| A (in vivo) | 29.99 | 44.31 | 52.87 | 85.49 | 98.90 | |
| B | 22.85 | 42.12 | 52.19 | 89.01 | 104.38 | |
| C | 35.16 | 48.68 | 57.86 | 74.06 | 86.16 | |
| D | 29.13 | 57.07 | 78.64 | 93.40 | 104.44 | |

The results are shown in FIG. 11. The results show that all compositions tested are able to maintain a pH decrease for at least 48 hours. The release of lactic acid from the compositions vary. Composition D seems to release lactic acid faster than the other compositions, but still in a prolonged fashion enabling a pH decrease for at least 48 hours. Accordingly, the choice of mucoadhesive polymer may have some impact on the release rate of lactic acid from the oligomers.

Example 16

Pharmaceutical Compositions Containing OMLA—Pessaries

Pessaries were prepared and used in a pilot in vivo study (see example 17) Moulded pessary [mg]:

| OMLA 30 | 500 |
|---|---|
| Macrogol 6000 | 2000 (prod. Hoechst) |

Macrogol 6000 (polyoxyethylene glycol m.w. 6000 Da) was melted at 50° C. and OMLA was admixed. The warm mass was transferred to the unit dose forms and left for cooling.
Variations

| | Quality | Quantity |
|---|---|---|
| I. Composition | | |
| OMLA 30 -- 20.0 (%) | OMLA 10-30, OMLA Lac2008.003; 007; 007; (+LA) | 2-50% |
| Macrogol 6000 -- 80% | other solid macrogols or their mixture with semisolid or liquid macrogols | 50%-98% |
| II. Size | | |
| Torpedo like Mass - 2.5 g | any shape suitable for vaginal application | up to 5 g |

| | Quality | Quantity |
|---|---|---|
| III. Preparation | | |
| Macrogol 6000 was melted at 50° C. and OMLA was admixed. | Temperature 40-100° C. may be applied | |
| The warm mass was transferred to the unit dose forms and left for cooling | The cooling may be fast. | |

Example 17

Pilot In Vivo Studies

Study performed in order to investigate different formulations of OMLA in comparison with two marketed drugs (Vivag and Lactal gel).

A prototype of a pessary (vagitorium, 500 mg) and a lyophylised vaginal tablet (400 mg) was used in a single dose self testing in-vivo experiment by a healthy female volunteer (age 56). The vaginal pH was monitored during 36 to 96 h. The results as can be seen in FIGS. 12A-12D, visualising the results from the use of the pessary composition (A), vaginal tablet (B), Lactal® gel (C, 225 mg LA) and Vivag® (D)) the OMLA formulations shows as much more prolonged effect of keeping a low pH in the vaginal tract compared to Lactal gel or Vivag which temporarily lowers the pH but does not otherwise display a persistence to keeping the pH at low levels. With the OMLA vaginal tablet the low pH levels could be detected up to 72 h with no subjective discomfort reported. With the OMLA pessary an even more prolonged effect could be seen with only minor discomfort reported. Thus the pH-lowering effect persisted up to 60-80 h confirming the expected mucoadhesive properties as well as good subjective tolerability. The individual formulations were monitored as can be seen in the tables below;

| A OMLA30 Pessary | | B OMLA30 vaginal tablet | | Lactal ® gel (225 mg LA) | | Vivag ® | |
|---|---|---|---|---|---|---|---|
| t (h) | pH | t (h) | pH | t (h) | pH | t (h) | pH |
| 0 | 4.4 | 0 | 4.4 | 0 | 4.4 | 0 | 4.4 |
| 4 | 3.6 | 4 | 4.1 | 4 | 3.6 | 4 | 4.7 |
| 8 | 3.6 | 8 | 3.6 | 8 | 4.1 | 8 | 4.4 |
| 12 | 4.1 | 12 | 3.6 | 12 | 4.4 | 12 | 4.4 |
| 24 | 4.1 | 24 | 3.6 | 24 | 4.4 | 24 | 4.1 |
| 28 | 4.1 | 28 | 3.6 | | | 28 | 4.4 |
| 32 | 4.1 | 32 | 3.6 | | | | |
| 36 | 4.1 | 36 | 3.6 | | | | |
| 48 | 4.1 | 48 | 4.1 | | | | |
| 52 | 4.1 | 52 | 4.1 | | | | |
| 56 | 4.1 | 56 | 4.1 | | | | |
| 60 | 4.1 | 60 | 4.1 | | | | |
| 72 | 4.1 | 72 | 4.4 | | | | |
| 76 | 4.1 | 76 | 4.4 | | | | |
| 80 | 4.25 | 80 | 4.4 | | | | |
| 84 | 4.4 | 84 | 4.4 | | | | |
| 96 | 4.4 | 96 | 4.4 | | | | |

In A: Discomfort: Day 1; Mild Burning and Discharge. Day 2; Mild Discharge. Day 3-5;
No subjective discomfort.
Tolerability: Mild discomfort
Acceptability: Good but not optimal
In B: Discomfort: Day 1-5; No Subjective Discomfort.
Tolerability: Very good.
Acceptability: Very good.
In C: Discomfort: Day 1; Mild Burning and Discharge. Day 2; No Discomfort.
Tolerability: Good.
Acceptability: Good.
In D: Discomfort: Day 1; No Discomfort.
Tolerability: Good.
Acceptability: Good.

Example 18

Clinical Study Protocol

A clinical development programme is initiated to demonstrate the utility of OMLA in BV and related diseases. In an initial study, a group of healthy postmenopausal consenting female subjects will be studied. A primary objective will be to evaluate tolerability and subject acceptability of different galenic formulations of lactate oligomer formulations in comparison with marketed products such as Vivag and Lactal gel. An additional objective is to investigate the safety aspect of the galenic lactate oligomer formulations.

Overall Study Design. The study will be conducted as a single-centre, trial in healthy peri-and/or postmenopausal women. At pre-entry, the subjects will undergo a gynaecological and clinical examination including medical history, vital signs and urianalysis within 10 days before the first study day. During the study period, the subjects will assess tolerability and acceptability score as well as conduct assessment of vaginal pH. Study lactate preparations will be dispensed at visit 1. Study parameters are; tolerability, acceptability and pH self-measurements. The different OMLA and control preparation administrations ill be separated by at least 1 week. A safety follow-up, including physical examination and urinanalysis will be performed 2-10 days after the last lactate vaginal application.

Description of Study Medication. The study preparations will be supplied in a vaginal pessary or tablet (with lactic acid) form of 400-600 mg of lactate equivalents. The formulations will contain excipients which are commonly used (PhEur) in vaginal preparations: hydroxyethylcellulose, macrogol. All subjects will receive 1-5 preparations over time (maximum 5 weeks) separated by at least 7 days. The study medication will be provided to the investigational site with batch/packaging numbers, certificate of analysis and expiry/retest dates.
Active compound: Lactate oligomer
Dosage form: Pessary or tablet
Strength: 400 mg and 600 mg (lactate equivalents)
Manufacturer: Pharmaceutical Faculty, University of Gdansk, Poland
Analysis: Microbial test and quality control tests according to Ph. Eur. (category 2)
Dosage regimens of study drugs Each subject will over time, separated by at least 7 days receive a maximum of 5 different single galenic formulations of the study preparation (lactate equivalents 400-600 mg). Marketed products such as Vivag and Lactal gel will serve as controls.

Duration of treatment. The duration of the study will be 4-8 weeks including pre-entry, study periods and follow-up.

Randomisation procedure. The subjects will be assigned treatment in an open design.

No blinding will be made

Assessment of data. The subjects will assess tolerability and acceptability score as well as conduct self-assessment of pH.

A full clinical development programme will be performed according to regulatory requirements.
Specific Embodiments 1. Use of one or more oligomers of lactic acid for the preparation of a formulation for the prophylaxis and/or treatment of gynaecological infections.

2. Use according to item 1, wherein the infection is a bacterial infection, such as bacterial vaginosis, unspecific colpitis, senile colpitis, cervicitis, and urethritis.

3. Use according to item 1, wherein the infection is a fungal infection, such as candidosis (*candida albicans*), cryptococcosis, actinomycosis.

4. Use according to item 1, wherein the infection is a viral infection, such as Human Immunodefiency Virus (HIV), Herpes Simplex Virus (HSV), Human Papilloma Virus (HPV).

5. Use according to item 1, wherein the one or more oligomers of lactic acid has the following formula II $$\text{ROC}\underset{}{\overset{}{\left[\begin{array}{c}\\O\end{array}\right]_n}}\text{OH} \quad (II)$$

wherein n is an integer from 1 to 20 such as, e.g., from 2 to 20, from 3 to 20, from 1 to 15, from 2 to 15, from 3 to 15, from 1 to 10, from 2 to 10, from 3 to 10, or from 4 to 9, wherein R is $R^1R^2N—$, $R^1O—$, or $R^1S—$,
$R^1$, $R^2$ and $R^3$ are the same or different and selected from H, $C_1$-$C_6$ alkyl including methyl, ethyl, propyl, isopropyl, butyl, isobutyl, tert. butyl, pentyl, hexyl, or aryl including benzyl,
and pharmaceutically acceptable salts thereof.

6. Use according to any one of the preceding items, wherein one or more oligomers of lactic acid have an inherent viscosity at 25° C. in the range of $10^{-3}$ to $10^{12}$ Pa·s, such as $10^{-1}$ to $10^9$ Pa·s, 1 to $10^5$ Pa·s, when determined by a rheometer.

7. Use according to any of the preceding items, wherein the one or more oligomers of lactic acid release lactic acid over a time period of at least 8 hours, at least 12 hours, such as at least 16 hours, at least 20 hours, at least 24 hours, at least 36 hours, at least 2 days, at least 3 days, at least 4 days, at least 5 days, at least 6 days, or at least 7 days when exposed to water at room temperature.

8. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a trimer of lactic acid (n=2).

9. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a tetramer of lactic acid (n=3).

10. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a pentamer of lactic acid (n=4).

11. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a hexamer of lactic acid (n=5).

12. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a heptamer of lactic acid (n=6).

13. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a octamer of lactic acid (n=7).

14. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a nonamer of lactic acid (n=8).

15. Use according to any of the preceding items, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a decamer of lactic acid (n=9).

16. Use according to any of the preceding items, wherein the formulation comprises at least 0.01% w/w of the one or more oligomers of lactic acid.

17. Use according to any of the preceding items, wherein the formulation comprises from about 0.02% to 100% w/w such as, e.g. from about 0.1% to about 95% w/w, from about 1% to about 95% w/w, from about 5% to about 95% w/w, from about 10% to about 90% w/w, from about 15% to about 90% w/w of the one or more oligomers of lactic acid.

18. Use according to any of the preceding items, wherein the formulation is designed for vaginal administration.

19. Use according to any of the preceding items, wherein the formulation is a solid, semi-solid or liquid formulation.

20. Use according to any of the preceding items, wherein the galenic formulation is in the form of a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal shaum, vaginal disc, semipermeable packaging and any combination thereof.

21. Use according to any of the preceding items, wherein the formulation further comprises one or more pharmaceutically acceptable excipients.

22. Use according to item 21, wherein the one or more pharmaceutically acceptable excipients are selected from the group consisting of cellulose derivatives such as hydroxypropyl methylcellulose (HPMC), methyl cellulose, hydroxyethyl cellulose (HEC), hydroxypropyl cellulose (HPC), ethyl hydroxyethyl cellulose, carboxymethyl cellulose and sodium carboxymethyl cellulose (Na CMC), starch derivatives such as moderately cross-linked starch, acrylic polymers such as carbomer and its derivatives (Polycarbophyl, Carbopol®, etc); polyethylene oxide (PEO), chitosan (poly-(D-glucosamine); natural polymers such as gelatin, sodium alginate, pectin, scleroglucan, tragacanth, gellan, xanthan gum or guar gum, poly co-(methylvinyl ether/maleic anhydride), microcrystalline cellulose/Avicel®), and crosscarmellose.

23. Use according to item 22, wherein the concentration of one or more pharmaceutically acceptable excipients are in the range 0.05 to 10 weight percent, such as 0.1 to 5 weight percent, of the formulation.

24. Use according to item 22 or 23, wherein the one or more pharmaceutically acceptable excipients are vaginal mucoadhesive promoting agents and/or viscosity-adjusting agents.

25. Use according to any of the preceding items, wherein the formulation further comprises one or more antiadhesion agents.

26. Use according to item 25, wherein the amount of antiadhesion agent is in the range 0.01 to 10 weight percent, such as 0.1 to 5 weight percent, of the formulation.

27. Use according to any of the preceding items, wherein the formulation comprises one or more further antimicrobial agents.

28. Use according to item 27, wherein the antimicrobial agent is selected from the group consisting of antibiotics, such as clindamycin or metronidazol, essential oils, such as tea tree oil, cations or elements, such as Hg, Cu, Pb, or Ag, polyene antimycotic, imidazole, triazole, allyamines, echinocandin, aciclovir, amantadine, alcohols, quartenary ammmonium compounds, boric acid, chlorhexidine gluconate, hydrogen peroxide, urea hydrogen peroxide, iodine, mercurochrome, octenine dihydrochloride, phenolic(carbolic acid) compounds, sodium chloride, sodium hypochlorite, nonoxynol, and any combination thereof.

29. An oligomer of lactic acid with the following formula I

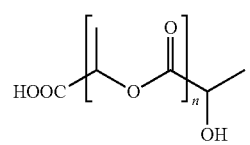

wherein n is an integer from 2 to 20 such as, e.g., from 3 to 20, from 2 to 15, from 3 to 15, from 2 to 10, from 3 to 10, from 4 to 10, or from 4 to 9.

30. An oligomer according to item 29, with the proviso that the oligomer is not a tetramer of lactic acid manufactured as described in the following: To a solution of lactic acid tetramer tert-butyl ester (0.6982 g) (1.9268 mmol) in methylene chloride (25 ml) was dropped a mixed solution of trifluoroacetic acid (2.5 ml) and methylene chloride (2.5 ml), followed by stirring at room temperature for 1 hour after the end of dropping; a saturated sodium hydrogen carbonate solution (30 ml) was added to adjust the pH of water layer to pH 8, and then a saturated ammonium chloride (50 ml) was added thereto to adjust the pH of water layer to pH 6; the resultant was extracted three times with diethyl ether (100 ml); the extraction solution contained almost all impurities and a small amount of the substance of interest; to the remaining water layer was dropped 1N hydrochloric acid (5 ml) cooled at 0° C., so as to adjust the pH of water layer to pH 2-3; the layer was extracted three times with methylene chloride (150 ml); at this time, the pH changed, and therefore 1N hydrochloric acid cooled at 0° C. was used to keep the pH of the water layer at pH 2-3; the resultant was dried over anhydrous magnesium sulphate day and night, concentrated, and isolated by column chromatography (developing solvent: hexane:diethyl ether=1:4) to obtain lactic acid tetramer (0.2047 g) (yield:34.7%) as a colourless oil.

31. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a trimer of lactic acid (n=2).

32. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a tetramer of lactic acid (n=3).

33. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a pentamer of lactic acid (n=4).

34. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a hexamer of lactic acid (n=5).

35. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a heptamer of lactic acid (n=6).

37. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a octamer of lactic acid (n=7).

38. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a nonamer of lactic acid (n=8).

39. An oligomer of lactic acid according to item 29 or 30, wherein at least 25% w/w such as, at least 30% w/w, at least 40% w/w, at least 50% w/w, at least 60% w/w, at least 70% w/w, at least 80% w/w or at least 90% w/w of the one or more oligomers of lactic acid is a decamer of lactic acid (n=9).

40. A formulation comprising one or more oligomers of lactic acid as defined in any of items 1-39 and one or more pharmaceutically acceptable excipients.

41. A formulation according to item 40, wherein the formulation comprises i) one or more oligomers of lactic acid or derivative thereof as defined in any of items 1-40, ii) a combination of one or more oligomers of lactic acid or derivative thereof as defined in any of items 1-40, or iii) a combination of i) and/or ii) and/or lactic acid for the prophylaxis and/or treatment of a microbial infection according to any of items 1-4.

41. A formulation according to item 39 or 40, wherein for the formulation is for intravaginal or transvaginal administration.

42. A formulation according to any of items 39-41, which further comprises an antibacterial agent selected from the group consisting of clindamycin, tetracycline, amoxicillin, ampicillin, erythromycin, doxycycline, lumefloxacin, norfloxacin, afloxam, ciproflaxin, azitromycin, cefltoxine.

43. A formulation according to any of the items 39-42, wherein the formulation further comprises a formulation of one or more antibacterial agents for the prophylaxis and/or treatment of gynaecological infections as defined in items 1-4.

44. A formulation according to item 45, wherein the antibacterial agent is selected from the group consisting of clindamycin, tetracycline, amoxicillin, ampicillin, erythromycin, doxycycline, lumefloxacin, norfloxacin, afloxam, ciproflaxin, azitromycin, cefltoxine.

45. A formulation according to item 43 or 44, wherein the amount of antibacterial agent is in the range from 5 mg to 1000 mg per dose.

46. A formulation according to any of the items 43-45, wherein the antibacterial agent selected from the group consisting of tetracycline, doxycycline, azithromycin, or erythromycin is incorporated into a tampon.

47. A formulation according to any of the items 39-46, wherein the formulation further comprises one or more broad spectrum antibiotic agent.

48. A formulation according to item 47, wherein the broad spectrum antibiotic agent is selected from the group consisting of clindamycin, tetracycline, amoxicillin, ampicillin, erythromycin, doxycycline, lumefloxacin, norfloxacin, afloxam, ciproflaxin, azithromycin, cefltoxine for the prophylaxis and/or treatment of gonorrhea or chlamydial infections.

49. A formulation according to item 48, wherein the amount of broad spectrum antibiotic agent is in the range from 100 mg to 3000 mg per dose.

50. A formulation according to any of the items 47-49, wherein the broad spectrum antibiotic agent is selected from the group consisting of tetracycline, amoxicillin, ampicillin, lumefloxacin, norfloxacin, afloxam, ciproflaxin, azithromycin or cefitoxine for prophylaxis and/or treatment of gonorrhea.

51. A formulation according to item 50, wherein the amount of broad spectrum antibiotic agent is in the range from 400 mg to 3000 mg per dose.

52. A formulation according to item 50 or 51, wherein the formulation is in the form of a tampon.

53. A formulation according to any of items 47-52, wherein the formulation further one or more broad spectrum antibiotic agents selected from the group consisting of tetracycline, doxycycline, and erythromycin for treatment of chlamydial infections.

54. A formulation according to item 53, wherein the amount of broad spectrum antibiotic agent is in the range from 100 mg to 2000 mg per dose.

55. A formulation according to item 53 or 54, wherein the formulation is in the form of a tampon.

56. A formulation according to any of items 39-55, which further comprises an antichlamydial agent selected from the group consisting of tetracycline, doxycycline, and erythromycin.

57. A formulation according to any of items 39-56, which further comprises an antifungal agent selected from the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole.

58. A formulation according to item 57, wherein the amount of antifungal agent per dose is in the range from 0.1 mg to 2000 mg for treatment of candidiasis.

59. A formulation according to item 57 or 58, wherein one or more antifungal agents selected from the group consisting of ketoconazole, miconazole and metronidazole and optionally, the agent is incorporated into a tampon.

60. A formulation according to any of items 39-59, which further comprises an antiviral agent selected from the group consisting of acyclovir, femciclovir, valacyclovir, and AZT.

61. A formulation according to any of the items 39-60, wherein the formulation further comprises an antiviral agent.

62. A formulation according to item 61, wherein the antiviral agent is selected from the group consisting of acyclovir, femciclovir, valacyclovir, and AZT.

63. A formulation according to item 61 or 62, wherein the amount of antiviral agent is in the range from 100 mg to 1200 mg per dose.

64. A formulation according to any of the items 61-63, wherein the antiviral agent is acyclovir and is incorporated into a tampon.

65. A formulation according to any of items 39-64, which further comprises an trichomonicidal or parasiticidal agent selected from the group consisting of metronidazole and clotrimazol.

66. A formulation according to any of the items 39-65, wherein the formulation further comprises metronidazole for treatment of trichomoniasis.

67. A formulation according to item 66, wherein the amount of metronidazole is in the range from 10 mg to 750 mg per dose.

68. A formulation according to any of items 39-67, wherein the pharmaceutically acceptable excipient is a lipophilic or hydrophilic carrier.

69. A formulation according to item 39-68 for intravaginal delivery, which comprises one or more lipophilic or hydrophilic carriers and one or more mucoadhesive agents in total concentrations in the range from 60 to 90% w/w and from 5 to 25% w/w, respectively.

70. A formulation according to item 39-69 for transvaginal delivery, which comprises one or more lipophilic or hydrophilic carriers, one or more mucoadhesive agents, and one or more penetration enhancers or sorption promoters in total concentrations in the range from 60 to 90% w/w, from 5 to 25% w/w, and from 5 to 20% w/w, respectively.

71. A formulation according to any of the items 39-70, wherein the formulation further comprises one or more lipophilic carriers of semi-synthetic glycerides of saturated fatty acids of 8-18 carbon atoms.

72. A formulation according to any of the items 39-71, wherein the formulation further comprises the hydrophilic carrier polyethylene glycol of a molecular weight from 400 to 6000.

73. A formulation according to any of the items 39-72, wherein the concentration of polyethylene glycol is in the range from 60 to 90% w/w.

74. A formulation according to any of the items 39-73, wherein the formulation further comprises the mucoadhesive agents alginate, pectin, or hydroxypropyl methylcellulose.

75. A formulation according to any of the items 39-74, wherein the concentration of hydroxypropyl methylcellulose is in the range from 5 to 20% w/w.

76. A formulation according to any of the items 39-75, wherein the penetration enhancer is a surfactant, bile salt, or ethoxyglycol.

77. A formulation according to item 76, wherein the concentration of ethoxyglycol is in the range from 5 to 30% w/w.

78. A formulation according to any of the items 39-77, wherein the pharmaceutical agent is incorporated into the device as a controlled release drug delivery system.

79. A device for the delivery of a formulation as defined in any of items 39-78 for the prophylaxis and/or treatment of a gynaecological infection as defined in any of items 1-4.

80. A device according to item 79, wherein the device is intravaginal.

81. A device according to item 79 or 80, wherein the formulation is administered intravaginally or transvaginally.

82. A device according to any of the items 79-81, wherein the pharmaceutical agent is incorporated into the device as a controlled release drug delivery system.

83. A kit for the prophylaxis and/or treatment of gynaecological infections as defined in any of the items 1-4, which comprises at least a first and a second component, wherein the first component comprises a formulation as defined in any of items 39-78 and the second component comprises instructions for use of the formulation.

84. A kit according to item 83, wherein the first component comprises a formulation as defined in any of items 39-78 and the second component comprises means for administration of the formulation.

85. A kit according to item 84, wherein a further third component comprises instructions for use of the formulation.

86. Kit according to item 84 or 85, wherein the formulation is in the form of a vaginal device and the means for administration is an applicator.

87. A package or container for storage of a kit as defined in any of the items 83-86.

88. A method for the prophylaxis and/or treatment of a gynaecological infection, the method comprising administering to a subject in need thereof an effective dose of one or more oligomers of lactic acid as defined in any of items 29-38, optionally in form of a formulation as defined in any of items 39-78.

89. A method for the management, prophylaxis and/or treatment of odour from vaginal discharge, the method comprising administering to a subject in need thereof an effective dose of one or more oligomers of lactic acid ad defined in any of items 29-38, optionally in form of a formulation as defined in any of items 39-78.

90. A method according to item 89, wherein the formulation is a sanitary device.

The invention claimed is:

1. A method for treating a subject suffering from or susceptible to bacterial vaginosis the method comprising: vaginally administering to the subject oligomeric lactic acid, wherein the total concentration of dimeric lactic acid (HL2), trimeric lactic acid (HL3), tetrameric lactic acid (HL4) and pentameric lactic acid (HL5) is about 30% w/w or higher.

2. The method of claim 1 wherein the administering establishes a low pH in the diseased environment.

3. The method of claim 1 wherein the oligomeric lactic acid has the following formula I

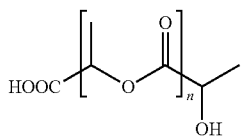

wherein n is an integer from 2 to 25.

4. The method of claim 1 wherein the oligomeric lactic acid has an average weight molecular weight of from about 300 to about 2,000.

5. The method of claim 1 wherein the oligomeric lactic acid has an inherent viscosity at 25° C. in the range of $10^{-3}$ to $10^{12}$ Pa·s when determined by a rheometer.

6. The method of claim 1 wherein the oligomeric lactic acid releases lactic acid over a time period of at least 8 hours when exposed to water at room temperature.

7. The method of claim 1 wherein a pharmaceutical composition is administered to the subject that comprises at least 0.01% w/w of the oligomeric lactic acid.

8. The method of claim 1 wherein a pharmaceutical composition comprising oligomeric lactic acid is administered and the pharmaceutical composition is in the form of a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal shaum, vaginal disc, semipermeable packaging or any combination thereof.

9. The method of claim 1 wherein a pharmaceutical composition comprising the oligomeric lactic acid is administered and the pharmaceutical composition further comprises one or more pharmaceutically acceptable excipients selected from the group consisting of cellulose derivatives, hydroxypropyl methylcellulose (HPMC), methyl cellulose, hydroxyethyl cellulose (HEC), hydroxypropyl cellulose (HPC), ethyl hydroxyethyl cellulose, carboxymethyl cellulose and sodium carboxymethyl cellulose (Na CMC), starch derivatives, moderately cross-linked starch, acrylic polymers, carbomer and its derivatives (Polycarbophyl, Carbopol®), polyethylene oxide (PEO), chitosan (poly-(D-glucosamine), natural polymers gelatin, sodium alginate, pectin, scleroglucan, tragacanth, gellan, xanthan gum or guar gum, poly co-(methylvinyl ether/maleic anhydride), microcrystalline cellulose/ Avicel®), and crosscarmellose.

10. The method of claim 8 wherein the concentration of the oligomeric lactic acid is from 1 to 50% w/w.

* * * * *